US012370188B2

(12) United States Patent
Bastin et al.

(10) Patent No.: US 12,370,188 B2
(45) Date of Patent: Jul. 29, 2025

(54) FORMULATIONS OF DAZUCORILANT, A GLUCOCORTICOID RECEPTOR MODULATOR

(71) Applicant: Corcept Therapeutics Incorporated, Redwood City, CA (US)

(72) Inventors: Rick Bastin, Menlo Park, CA (US); Alla Hosny, Nottingham (GB); Dolly Jacob, Nottingham (GB); Wu Lin, Nottingham (GB)

(73) Assignee: Corcept Therapeutics Incorporated, Redwood City, CA (US)

( * ) Notice: Subject to any disclaimer, the term of this patent is extended or adjusted under 35 U.S.C. 154(b) by 45 days.

(21) Appl. No.: 18/481,549

(22) Filed: Oct. 5, 2023

(65) Prior Publication Data

US 2024/0131020 A1    Apr. 25, 2024

Related U.S. Application Data

(60) Provisional application No. 63/378,578, filed on Oct. 6, 2022.

(51) Int. Cl.
*A61K 31/4745* (2006.01)
*A61K 9/48* (2006.01)
*A61K 47/10* (2017.01)
*A61K 47/22* (2006.01)

(52) U.S. Cl.
CPC ........ *A61K 31/4745* (2013.01); *A61K 9/4825* (2013.01); *A61K 9/4858* (2013.01); *A61K 9/4866* (2013.01); *A61K 47/10* (2013.01); *A61K 47/22* (2013.01)

(58) Field of Classification Search
CPC .. A61K 9/4825; A61K 31/4745; A61K 47/10; A61K 47/22
See application file for complete search history.

(56) References Cited

U.S. PATENT DOCUMENTS

| | | |
|---|---|---|
| 4,501,890 A | 2/1985 | Nichols et al. |
| 4,963,558 A | 10/1990 | Hotten et al. |
| 5,696,127 A | 12/1997 | Jones et al. |
| 6,166,013 A | 12/2000 | Coghlan et al. |
| 6,531,481 B2 | 3/2003 | Carroll et al. |
| 6,583,180 B2 | 6/2003 | Link et al. |
| 6,680,310 B2 | 1/2004 | Belanoff et al. |
| 6,716,856 B1 | 4/2004 | Pevarello et al. |
| 7,576,076 B2 | 8/2009 | Clark et al. |
| 7,678,813 B2 | 3/2010 | Clark et al. |
| 7,790,745 B2 | 9/2010 | Yang et al. |
| 7,799,782 B2 | 9/2010 | Munson et al. |
| 7,928,237 B2 | 4/2011 | Clark et al. |
| 8,003,689 B2 | 8/2011 | Veverka |
| 8,173,674 B2 | 5/2012 | Keil et al. |
| 8,324,203 B2 | 12/2012 | Clark et al. |
| 8,461,172 B2 | 6/2013 | Clark et al. |
| 8,518,961 B2 | 8/2013 | Ottinger |
| 8,598,154 B2 | 12/2013 | Clark et al. |
| 8,658,128 B2 | 2/2014 | Altschul et al. |
| 8,685,973 B2 | 4/2014 | Clark et al. |
| 8,710,035 B2 | 4/2014 | Pan et al. |
| 8,859,774 B2 * | 10/2014 | Hunt .................. A61K 31/4745 546/82 |
| 8,889,867 B2 | 11/2014 | Clark et al. |
| 8,969,557 B2 | 3/2015 | Harriman et al. |
| 9,107,926 B2 | 8/2015 | Belvin et al. |
| 9,114,147 B2 | 8/2015 | Altschul et al. |
| 9,149,485 B2 | 10/2015 | Pan et al. |
| 9,273,047 B2 | 3/2016 | Hunt et al. |
| 9,289,436 B2 | 3/2016 | Szmulewitz et al. |
| 9,314,473 B2 | 4/2016 | Altschul et al. |
| 9,320,747 B1 | 4/2016 | Altschul et al. |
| 9,422,323 B2 | 8/2016 | Houpis et al. |
| 9,623,032 B2 | 4/2017 | Pan et al. |
| 9,707,223 B2 | 7/2017 | Hunt et al. |
| 9,801,893 B2 | 10/2017 | Szmulewitz et al. |
| 9,829,495 B2 | 11/2017 | Moraitis |
| 9,943,505 B2 | 4/2018 | Hunt et al. |
| 9,956,216 B2 | 5/2018 | Hunt et al. |
| 10,047,082 B2 | 8/2018 | Hunt et al. |
| 10,117,852 B2 | 11/2018 | Hunt et al. |
| 10,213,414 B2 | 2/2019 | Hunt et al. |
| 10,323,034 B2 | 6/2019 | Hunt et al. |
| 10,413,540 B2 | 9/2019 | Hunt |
| 10,449,178 B2 | 10/2019 | Hunt et al. |
| 10,456,392 B2 | 10/2019 | Hunt et al. |

(Continued)

FOREIGN PATENT DOCUMENTS

| | | | |
|---|---|---|---|
| JP | H09505030 A | 5/1997 | |
| WO | 9504734 A1 | 2/1995 | |

(Continued)

OTHER PUBLICATIONS

Hunt et al.; "1H-Pyrazolo[3,4-g]hexahydro-isoquinolines as potent GR antagonists with reduced hERG inhibition and an improved pharmacokinetic profile"; 2015; Bioorganic & Medicinal Chemistry Letters; 25:5720-5725 (Year: 2015).*
Yang et al.; "Recent Advances in the Application of Vitamin E TPGS for Drug Delivery"; 2018; Theranostics; 8(2): 464-485 (Year: 2018).*
Pineau et al., "New selective glucocorticoid receptor modulators reverse amyloid-β peptide-induced hippocampus toxicity", Nuerobiology of aging, 2016, vol. 45, pp. 109-122.
International Search Report and Written Opinion, Application No. PCT/US2023/069188, dated Oct. 30, 2023.
International Search Report and Written Opinion, Application No. PCT/US2023/076130, dated Feb. 5, 2024,.

(Continued)

*Primary Examiner* — Timothy P Thomas
(74) *Attorney, Agent, or Firm* — Mintz, Levin, Cohn, Ferris, Glovsky and Popeo, P.C.

(57) ABSTRACT

The present invention provides formulations of (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone, and methods of making and using the same.

10 Claims, No Drawings

(56) References Cited

U.S. PATENT DOCUMENTS

| | | |
|---|---|---|
| 10,568,880 B2 | 2/2020 | Hunt |
| 10,646,474 B2 | 5/2020 | Hunt et al. |
| 10,787,449 B2 | 9/2020 | Hunt et al. |
| 10,828,280 B2 | 11/2020 | Hunt et al. |
| 10,898,478 B2 | 1/2021 | Hunt |
| 10,973,813 B2 | 4/2021 | Hunt et al. |
| 11,370,789 B2 | 6/2022 | Hunt et al. |
| 11,464,764 B2 | 10/2022 | Scott et al. |
| 11,576,907 B2 | 2/2023 | Hunt et al. |
| 11,648,245 B2 | 5/2023 | Hunt et al. |
| 2002/0115613 A1 | 8/2002 | Kumar |
| 2003/0064974 A1 | 4/2003 | Belanoff |
| 2004/0102422 A1 | 5/2004 | Gaston |
| 2004/0229855 A1 | 11/2004 | Belanoff |
| 2005/0085464 A1 | 4/2005 | Sapse et al. |
| 2005/0124533 A1 | 6/2005 | Schatzberg et al. |
| 2005/0245588 A1 | 11/2005 | Ali et al. |
| 2006/0063748 A1 | 3/2006 | Belanoff |
| 2007/0128627 A1 | 6/2007 | Simons et al. |
| 2007/0203179 A1 | 8/2007 | Clark et al. |
| 2007/0281928 A1 | 12/2007 | Clark et al. |
| 2008/0070950 A1 | 3/2008 | Benjamin et al. |
| 2008/0287419 A1 | 11/2008 | Bruncko et al. |
| 2009/0156672 A1 | 6/2009 | Budunova et al. |
| 2010/0135956 A1 | 6/2010 | Gant et al. |
| 2010/0179115 A1 | 7/2010 | Belanoff |
| 2010/0292477 A1 | 11/2010 | Clark et al. |
| 2011/0166110 A1 | 7/2011 | Clark et al. |
| 2011/0166115 A1 | 7/2011 | Belanoff |
| 2011/0269728 A1 | 11/2011 | Pan et al. |
| 2012/0022121 A1 | 1/2012 | Dalton et al. |
| 2012/0201747 A1 | 8/2012 | Altschul et al. |
| 2012/0220565 A1 | 8/2012 | Clark et al. |
| 2013/0225633 A1 | 8/2013 | Hunt et al. |
| 2014/0005158 A1 | 1/2014 | Belanoff |
| 2014/0038926 A1 | 2/2014 | Hunt et al. |
| 2015/0080389 A1 | 3/2015 | Hunt et al. |
| 2015/0196640 A1 | 7/2015 | Cacase et al. |
| 2016/0215049 A1 | 7/2016 | Feldhaus et al. |
| 2017/0020860 A1 | 1/2017 | Hunt et al. |
| 2017/0045535 A1 | 2/2017 | Moraitis |
| 2017/0273972 A1 | 9/2017 | Hunt et al. |
| 2018/0125856 A1 | 5/2018 | Moraitis et al. |
| 2018/0193313 A1 | 7/2018 | Hunt et al. |
| 2018/0280378 A1 | 10/2018 | Hunt |
| 2018/0325891 A1 | 11/2018 | Scott et al. |
| 2019/0076424 A1 | 3/2019 | Hunt |
| 2020/0197372 A1* | 6/2020 | Scott .................. A61K 47/14 |
| 2021/0169872 A1 | 6/2021 | Hunt et al. |
| 2021/0308893 A1 | 10/2021 | Caboni |
| 2021/0369701 A1 | 12/2021 | Hunt et al. |
| 2022/0227753 A1 | 7/2022 | Dener et al. |
| 2023/0416250 A1 | 12/2023 | Hunt |

FOREIGN PATENT DOCUMENTS

| | | |
|---|---|---|
| WO | 9945925 A1 | 9/1999 |
| WO | 0069846 A1 | 11/2000 |
| WO | 03015692 A2 | 2/2003 |
| WO | 03061651 A1 | 7/2003 |
| WO | 2005087769 A1 | 9/2005 |
| WO | 2009064738 A2 | 5/2009 |
| WO | 2011113015 A2 | 9/2011 |
| WO | 2012027702 A1 | 3/2012 |
| WO | 2013039916 A1 | 3/2013 |
| WO | 2013177559 A2 | 11/2013 |
| WO | 2015077530 A1 | 5/2015 |
| WO | 2016014365 A1 | 1/2016 |
| WO | 2016055533 A1 | 4/2016 |
| WO | 2016141365 A1 | 9/2016 |
| WO | 2017023694 A1 | 2/2017 |
| WO | 2017151613 A1 | 9/2017 |
| WO | 2020132023 A1 | 6/2020 |
| WO | 2020172501 A1 | 8/2020 |
| WO | 2020190351 | 9/2020 |
| WO | 2021163058 | 8/2021 |
| WO | 2022134033 A1 | 6/2022 |
| WO | 2022140600 A1 | 6/2022 |
| WO | 2024006773 | 1/2024 |

OTHER PUBLICATIONS (2017) Capryol® 90—Propylene glycol monocaprylate type II, Accessed Nov. 14, 2021. First made available to public on May 28, 2017. Available from :<https://www.gattefosse.com/pharmaceuticals-products/capryol-90 >, 4 pages.

Extended European Search Report for Application No. EP09774351.2, mailed on dated May 7, 2012, 7 pages.

Extended European Search Report for Application No. EP19188885.8, mailed on dated Oct. 28, 2019, 6 pages.

Extended European Search Report received for EP19898009.6, mailed on Sep. 8, 2022, 14 pages.

Extended European Search Report received for EP21154665.0, mailed on Apr. 23, 2021, 5 pages.

Extended European Search Report, Application No. EP13751132.5, mailed on dated Mar. 21, 2016, 6 pages.

Extended European Search Report, Application No. EP13793417.0, mailed on dated Jan. 4, 2016, 7 pages.

Extended European Search Report, Application No. EP16183642.4, mailed on dated Dec. 1, 2016 ., 12 pages.

Extended European Search Report, Application No. EP18154256.4, mailed on dated Mar. 26, 2018, 6 pages.

Extended European Search Report, Application No. EP18777520.0, mailed on dated Jul. 16, 2020, 9 pages.

International Preliminary Report on Patentability for Application No. PCT/US2013/027150, mailed on dated Sep. 4, 2014, 7 pages.

International Preliminary Report on Patentability For Patent Application No. PCT/US2019/067108, mailed on Jul. 1, 2021, 7 pages.

International Preliminary Report on Patentability, Application No. PCT/US2013/042732, mailed on dated Nov. 25, 2014, 5 pages.

International Search Report and Written Opinion for Application No. PCT/US2009/049273, mailed on dated Aug. 14, 2009, 7 pages.

International Search Report and Written Opinion for Application No. PCT/US2011/049408, mailed on dated Jan. 30, 2012, 10 pages.

International Search Report and Written Opinion for Application No. PCT/US2013/027150, mailed on dated Apr. 29, 2013, 9 pages.

International Search Report and Written Opinion for Application No. PCT/US2013/027720, mailed on dated Jun. 17, 2013, 8 pages.

International Search Report and Written Opinion for Application No. PCT/US2018/025547, mailed on dated Aug. 9, 2018, 11 pages.

International Search Report and Written Opinion for PCT Application No. PCT/US2019/067108, mailed on dated Jun. 25, 2020, 13 pages.

International Search Report and Written Opinion, Application No. PCT/CN2020/139524, mailed on dated Sep. 26, 2021, 15 pages.

International Search Report and Written Opinion, Application No. PCT/US2021/064947, mailed on dated Apr. 15, 2022, 16 pages.

International Search Report and Written Opinion, for Application No. PCT/US2010/034382, mailed on dated Jul. 9, 2010, 7 pages.

International Search Report for PCT Application No. PCT/US2005/0008049, mailed on dated Jun. 15, 2005., 8 pages.

International Search Report for PCT Application No. PCT/US2013/042732, mailed on dated Dec. 2, 2013, 4 pages.

Partial Supplementary European Search Report, Application No. EP13751132.5, mailed on dated Sep. 7, 2015, 4 pages.

(2005) Preservatives and Antioxidants Database—Compounding Today, Available at: <https://compoundingtoday.com/Preservative/>, 2 pages.

Study of Drug 1 (Enzalutamide) Plus Drug 2 (Relacorilant) for Patients With Prostate Cancer, ClinicalTrials.gov NCT03674814, 8 pages.

Study of Relacorilant in Combination with Nab-Paclitaxel for Patients with Recurrent Platinum-Resistant Ovarian, Fallopian Tube, or Primary Peritoneal Can, ClinicalTrials.gov, Available online at: https://clinicaltrials.gov/ct2/show/NCT03776812, 12 pages.

(56) References Cited

OTHER PUBLICATIONS

Study to Evaluate Cort125134 in Combination with Nab-Paclitaxel in Patients with Solid Tumors, ClinicalTrials.gov NCT02762981, 8 pages.
(Mar. 30, 2018) Substantive Examination Adverse Report, MYPI2014003289, 2 pages.
Aherne et al. (2002) "Finding the Needle in the Haystack: Why Highthroughput Screening is Good for Your Health", Breast Cancer Research, 4(4):148-154.
Aisen et al. (Feb. 8, 2000) "A Randomized Controlled Trial of Prednisone in Alzheimer's Disease. Alzheimer's Disease Cooperative Study", Neurology, 54(3):588-593.
Akiyama et al. (May-Jun. 2000) "Inflammation and Alzheimer's Disease", Neurobiol Aging, 21(3):383-421.
Antonarakis et al. (Sep. 2011) "Emerging Therapeutic Approaches in the Management of Metastatic Castration Resistant Prostate Cancer", Prostate Cancer and Prostatic Diseases, 14(3):206-218.
Arrat et al. (May 8, 2015) "ACTH (Acthar Gel) Reduces Toxic SOD1 Protein Linked to Amyotrophic Lateral Sclerosis in Transgenic Mice: A Novel Observation", PLoS One, 10(5):e0125638 (12 pages).
Attard et al. (Jun. 15, 2011) "Translating Scientific Advancement into Clinical Benefit for Castration-Resistant Prostate Cancer Patients", Clinical Cancer Research, 17(12):3867-3875.
Behl et al. (May 1997) "Protection Against Oxidative Stress-Induced Neuronal Cell Death—A Novel Role for RU486", European Journal of Neuroscience, 9(5):912-920.
Belanoff et al. (Mar. 25, 2011) "Selective glucocorticoid receptor (type II) antagonists prevent weight gain caused by olanzapine in rats", European Journal of Pharmacology, 655(1-3):117-120.
Belova et al. (Aug. 2009) "Glucocorticoid Receptor Expression in Breast Cancer Associates with Older Patient Age", Breast Cancer Research and Treatment, 116(3):441-447.
Benagiano et al. (Oct. 2008) "Selective Progesterone Receptor Modulators 3: Use in Oncology, Endocrinology and Psychiatry", Expert Opinion on Pharmacotherapy, 9(14):2487-2496.
Block et al. (Mar. 6, 2017) "Glucocorticoid Receptor Expression in 20 Solid Tumor Types Using Immunohistochemistry Assay", Cancer Management and Research, 9:65-72.
Bolton et al. (Aug. 2007) "Cell- and Gene-Specific Regulation of Primary Target Genes by the Androgen Receptor", Genes & Development, 21(16):2005-2017.
Bolton et al. (1989) "The Effects of the Anti-Glucocorticoid RU 38486 on Steroid-Mediated Suppression of Experimental Allergic encephalomyelitis (EAE) in the Lewis Rat", Life Sciences, 45(1):97-104.
Brusaferri et al. (Jun. 2000) "Steroids for Multiple Sclerosis and Optic Neuritis: A Meta-Abstract Analysis of Randomized Controlled Clinical Trials", Journal of Neurology, 247(6):435-442.
Caccamo et al. (Jan. 16, 2013) "Glucocorticoids Exacerbate Cognitive Deficits in TDP-25 Transgenic Mice Via a Glutathionemediated Mechanism: Implications for Aging, Stress and TDP-43 Proteinopathies", The Journal of Neuroscience, 33(3):906-913.
Carri et al. (Aug. 30, 2003) "Neurodegeneration in Amyotrophic Lateral Sclerosis: The Role of Oxidative Stress and Altered Homeostasis of Metals", Brain Research Bulletin, 61(4):365-374.
Chan et al. (Nov. 1, 2000) "Prognostic Significance of Gleason Score 3+4 versus Gleason Score 4+3 Tumor at Radical Prostatectomy", Adult Urology, 56(5):823-827.
Check et al. (May 2014) "Evidence that Mifepristone, A Progesterone Receptor Antagonist, Can Cross the Blood Brain Barrier and Provide Palliative Benefits for Glioblastoma Multiforme Grade IV", Anticancer Research, 34(5):2385-2388.
Check et al. (May 2014) "Mifepristone Causing Complete Remission of Rapidly Advancing Leukemia with Measurement of Progesterone-induced Blocking Factor", nticancer Research, 34(5):2413-2416.
Chen et al. (May 30, 1997) "Androgen and Glucocorticoid Receptor Heterodimer Formation. A Possible Mechanism for Mutual Inhibition of Transcriptional Activity", Journal of Biological Chemistry, 272(22):14087-14092.
Chen et al. (Feb. 27, 2014) "Mechanism of the Reversal Effect of Mifepristone on Drug Resistance of the Human Cervical Cancer Cell Line HELA/MMC", Genetics and Molecular Research, 13(1):1288-1295.
Chi et al. (Oct. 2009) "Castration-Resistant Prostate Cancer: From New Pathophysiology to New Treatment Targets", European Urology, 56(4):594-605.
Cho et al. (Mar. 8, 2005) "Role of Activation function Domain-1, DNA Binding, and Coactivator GRIP1 in the Expression of Partial Agonist Activity of Glucocorticoid Receptor-Antagonist Complexes", Biochemistry, 44(9):3547-3561.
Clark et al. (Feb. 15, 2008) "1H-Pyrazolo[3,4-g]Hexahydro-Isoguinolines as Selective Glucocorticoid Receptor Antagonists with High Functional Activity", Bioorganic & Medicinal Chemistry Letters, 18(4):1312-1317.
Clark Robind (2008) "Glucocorticoid Receptor Antagonists", Current Topics in Medicinal Chemistry, 8(9):813-838.
Cleutjens et al. (Dec. 1997) "Both Androgen Receptor and Glucocorticoid Receptor Are Able to Induce Prostate-Specific Antigen Expression, but Differ in Their Growth-Stimulating Properties of LNCaP Cells", Endocrinology, 138(12):5293-5300.
Colleoni et al. (Aug. 2000) "Response to Primary Chemotherapy in Breast Cancer Patients with Tumors Not Expressing Estrogen and Progesterone Receptors", Annals of Oncology, 11(8):1057-1059.
Cossu et al. (Jul. 2005) "The Role of Mifepristone in Meningiomas Management: A Systematic Review of the Literature", BioMed Research International, 2015:267831(11 pages).
Cummings et al. (2019) "Treatment Combinations for Alzheimer's Disease: Current and Future Pharmacotherapy Options", Journal of Alzheimer's Disease, 67(3):779-794.
Damia et al. (Nov. 2009) "Contemporary Pre-clinical Development of Anticancer Agents—What Are the Optimal Preclinical Models?", European Journal of Cancer, 45(16):2768-2781.
Davies et al. (Oct. 1990) "Association of Glucocorticoid Receptors with Prostate Nuclear Sites for Androgen Receptors and with Androgen Response Elements", Journal of Molecular Endocrinology, 5(2):117-127.
De-Bono et al. (May 26, 2011) "Abiraterone and Increased Survival in Metastatic Prostate Cancer", The New England Journal of Medicine, 364(21):1995-2005.
Desmedt et al. (Jun. 1, 2007) "Strong Time Dependence of the 76-Gene Prognostic Signature for Node-Negative Breast Cancer Patients in the TRANSBIG Multicenter Independent Validation Series", Clinical Cancer Research, 13(11):3207-3214.
Di-Lorenzo et al. (2010) "Castration-Resistant Prostate Cancer", Drugs, 70(8):983-1000.
Dinkel et al. (Feb. 2003) "Novel Glucocorticoid Effects on Acute Inflammation in the CNS", Journal of Neurochemistry, 84(4):705-716.
Donovan et al. (Feb. 2010) "Androgen Receptor Expression is Associated with Prostate Cancer-Specific Survival in Castrate Patients with Metastatic Disease", BJU International, 105(4):462-467.
Evans et al. (2014) "CNS-Targeted Glucocorticoid Reduces Pathology in Mouse Model of Amyotrophic Lateral Sclerosis", Acta Neuropathologica Communications, 2:66(13 pages).
Fakih et al. (Oct. 2002) "Glucocorticoids and Treatment of Prostate Cancer: A Preclinical and Clinical Review", Urology, 60(4):553-561.
Fidler et al. (Dec. 25, 2011) "Disease Progression in a Mouse Model of Amyotrophic Lateral Sclerosis: The Influence of Chronic Stress and Corticosterone", The FASEB Journal, 25(12):4369-4377.
Fiorentino et al. (Feb. 2010) "Blood and tissue biomarkers in prostate cancer: state of the art", Urologic Clinics of North America, 37(1):131-141.
Flexner Charles (Dec. 2007) "HIV Drug Development: The Next 25 Years", Nature Reviews, Drug Discovery, 6(12):959-966.
Gaddy et al. (Aug. 1, 2004) "Mifepristone Induces Growth Arrest, Caspase Activation, And Apoptosis Of Estrogen Receptor-

(56) References Cited

OTHER PUBLICATIONS

Expressing, Antiestrogen-Resistant Breast Cancer Cells", Clinical Cancer Research, 10(15):5215-5225.
Gargiulo-Monachelli et al. (Jun. 2014) "Circulating Gonadal and Adrenal Steroids in Amyotrophic Lateral Sclerosis: Possible Markers of Susceptibility and Outcome", Hormone and Metabolic Research, 46(6):433-439.
Ghoumari et al. (Jun. 2003) "Mifepristone (RU486) Protects Purkinje Cells from Cell Death in Organotypic Slice Cultures of Postnatal Rat and Mouse Cerebellum", Proceedings of the National Academy of Sciences, 100(13):7953-7958.
González Deniselle et al. (Feb. 1997) "Glucocorticoid Receptors and Actions in the Spinal Cord of the Wobbler Mouse, A Model for Neurodegenerative Diseases", Journal of Steroid Biochemistry and Molecular Biology, 60(3-4):205-213.
Grover et al. (Jul. 2002) "The Initiation of Breast and Prostate Cancer", Carcinogenesis, 23(7):1095-1102.
Gulliver (Mar. 2017) "Xenobiotics and the Glucocorticoid Receptor", Toxicology and Applied Pharmacology, 319:69-79.
Guo et al. (Mar. 2009) "A Novel Androgen Receptor Splice Variant Is Up-Regulated During Prostate Cancer Progression and Promotes Androgen Depletion-Resistant Growth", 69(6):2305-2313.
Han et al. (Feb. 2003) "Biochemical (Prostate Specific Antigen) Recurrence Probability Following Radical Prostatectomy for Clinically Localized Prostate Cancer", The Journal of Urology, 169(2):517-523.
He et al. (2015) "Discovery of a Highly Potent Glucocorticoid for Asthma Treatment", Cell Discovery, 1(15035):13 Pages.
Hein et al. (2008) "Click Chemistry, A powerful Tool for Pharmaceutical Sciences", Pharmaceutical Research, 25(10):2216-2230.
Hemmi et al. (2011) "Dramatic Response of Dropped Head Sign to Treatment with Steroid in Parkinson's Disease: Report of Three Cases", Internal Medicine, 50(7):757-761.
Henderson et al. (1998) "Estrogens as a Cause of Human Cancer: the Richard and Hinda Rosenthal Foundation Award Lecture", 48(2):246-253.
Ho et al. (1993) "A Complex Response Element in Intron 1 of the Androgen-Regulated 20-kDa Protein Gene Displays Cell Type-Dependent Androgen Receptor Specificity", Journal of Biological Chemistry, 268(36):27226-27235.
Huang et al. (2010) "Reversal Effect of Mifepristone on Adriamycin Resistance in Human Breast Cancer Cell Line MCF-7/ADM in Vitro and in Vivo", Journal of Central South University(Medical Sciences), 35(6):576-583.
Hunt et al. (2015) "1H-Pyrazolo[3,4-g]hexahydro-isoquinolines as potent GR antagonists with reduced hERG inhibition and an improved pharmacokinetic profile", Bioorganic & Medicinal Chemistry Letters, 25(24):5720-5725.
Hunt et al. (2017) "Abstract 3623: Preclinical Efficacy of the Selective GR Antagonist, CORT125134", American Association for Cancer Research, 4 pages.
Hunt et al. (May 2018) "Assessment of Safety, Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, 7(4):408-421.
Hunt et al. (Apr. 27, 2017) "Identification of the Clinical Candidate (R)-(1-(4-Fluorophenyl)-6-((1-Methyl-1H-Pyrazol-4-yl) Sulfonyl)-4,4a,5,6,7,8-Hexahydro-1H-Pyrazolo[3,4-g]lsoquinolin-4a-yl)(4-(Trifluoromethyl)Pyridin-2-yl) Methanone (CORT125134): A Selective Glucocorticoid Receptor", Journal of Medicinal Chemistry, 60(8):3405-3421.
Jannin et al. (2014) "Polyoxylglycerides and Glycerides: Effects of Manufacturing Parameters on API Stability, Excipient Functionality and Processing", International Journal of Pharmaceutics, 466(1-2):109-121.
Jemal et al. (2010) "Cancer Statistics", CA: A Cancer Journal for Clinicians, 60(5):277-300(25 Pages).

Johnson et al. (2001) "Relationships Between Drug Activity in NCI Preclinical in Vitro and in Vivo Models and Early Clinical Trial", British Journal of Cancer, 84(10):1424-1431.
Kach et al. (2015) "Glucocorticoid Receptor Signaling in Breast and Prostate Cancers: Emergence as a Therapeutic Target", Science Translational Medicine, 7(305):9 Pages.
Kach et al. (2017) "Selective Glucocorticoid Receptor Modulators (SGRMs) Delay Castrate-Resistant Prostate Cancer Growth", Molecular Cancer Therapeutics, 16(8):1680-1692.
Kadmiel et al. (2013) "Glucocorticoid Receptor Signaling in Health and Disease", Trends in Pharmacological Sciences, 34(9):518-530.
Keen et al. (2003) "The Biology of Breast Carcinoma", Cancer, 97(3 Suppl):825-833.
Kim et al. (2011) "Current Treatment Strategies for Castration-Resistant Prostate Cancer", Korean Journal of Urology, 52(3):157-165.
Klein et al. '(2007) "Analyzing Survival Curves at a Fixed Point in Time", Statistics in Medicine, 26(24):4505-4519.
Klijn et al. (1989) "Antiprogestins a New Form of Endocrine Therapy for Human Breast Cancer", Cancer Research, 49(11):2851-2856.
Kondo (2010) "A Case of Ectopic Adrenocorticotropic Hormone-Producing Pancreatic Neuroendocrine Tumor with Multiple Liver Metastases", Endocrine Journal, 57(3):229-236.
Koochekpour (2010) "Androgen Receptor Signaling and Mutations in Prostate Cancer", Asian Journal of Andrology, 12(5):639-657.
Kriaucionis et al. (2009) "The Nuclear DNA Base 5-Hydroxymethylcytosine is Present in Brain and Enriched in Purkinje Neurons", Science, 24(5929):929-930.
Lante et al. (2015) "Subchronic Glucocorticoid Receptor Inhibition Rescues Early Episodic Memory and Synaptic Plasticity Deficits in a Mouse Model of Alzheimer's Disease", Neuropsychopharmacology, 40(7):1772-1781.
Li et al. (2004) "High Level of Androgen Receptor is Associated with Aggressive Clinicopathologic Features and Decreased Biochemical Recurrence-Free Survival in Prostate: Cancer Patients Treated with Radical Prostatectomy", The American Journal of Surgical Pathology, 28(7):928-934.
Li et al. (2017) "Systemic Overexpression of the 11 B-HSD1 Promotes Endoplasmic Reticulum Stress in Multiple Tissues and the Development of Metabolic Syndrome in Mice", Molecular Medicine Reports, 16(5):7738-7744.
Loi et al. (2007) "Definition of Clinically Distinct Molecular Subtypes in Estrogen Receptor-Positive Breast Carcinomas Through Genomic Grade", Journal of Clinical Oncology, 25(10):1239-1246.
Loi et al. (2008) "Predicting Prognosis Using Molecular Profiling in Estrogen Receptor-Positive Breast Cancer Treated With Tamoxifen", BMC Genomics, 9(239):12 Pages.
Lotan et al. (2007) "Up-Regulation of MKK4, MKK6 and MKK7 During Prostate Cancer Progression: An Important Role for SAPK Signalling in Prostatic Neoplasia", The Journal of Pathology, 212(4):386-394.
Lucci et al. (1999) "Modification of Ceramide Metabolism Increases Cancer Cell Sensitivity to Cytotoxics", International Journal of Oncology, 15(3):541-546.
Ma et al. (2003) "IL-21 Activates Both Innate and Adaptive Immunity to Generate Potent Antitumor Responses that Require Perforin but Are Independent of IFN-Gamma", Journal of Immunology, 171(2):608-615.
Macpherson et al. (2005) "Glucocorticoids Worsen Excitotoxin-Induced Expression of Pro-Infammatory Cytokines in Hippocarnpal Cultures", Experimental Neurology, 194(2):376-383.
Makarov et al. (2007) "Updated Nomogram to Predict Pathologic Stage of Prostate Cancer Given Prostate-Specific Antigen Level, Clinical Stage, and Biopsy Gleason Score (Partin Tables) Based on Cases from 2000 to 2005", Urology, 69(6):1095-1101.
Melhem et al. (2009) "Administration of Glucocorticoids to Ovarian Cancer Patients is Associated with Expression of the Anti-apoptotic Genes SGK1 and MKP1/DUSP1 in Ovarian Tissues", Clinical Cancer Research, 15(9):3196-3204.
Meyer et al. (2018) "The Selective Glucocorticoid Receptor Modulator Cort 113176 Reduces Neurodegeneration and Neuroinflammation in Wobbler Mice Spinal Cord", Neuroscience, 384:384-396.

(56) References Cited

OTHER PUBLICATIONS

Meyer et al. (2014) "The Selective Glucocorticoid Receptor Modulator CORT108297 Restores Faulty Hippocampal Parameters in Wobbler and Corticosterone-Treated Mice", The Journal of Steroid Biochemistry and Molecular Biology, 143:40-48.
MIFEPREX (Jul. 19, 2005) "Mifepristone", Label, Rev 2, Available Online at: A96. http://web.archive.org/web/20060628212659/http://www.fda.gov/cder/foi/label/2005/020687s0131bl.pdf, 20 pages.
Mikosz et al. (2001) "Glucocorticoid Receptor-Mediated Protection from Apoptosis is Associated with Induction of the Serine/Threonine Survival Kinase Gene, sgk-1", The Journal of Biological Chemistry, 276(20):16649-16654.
Miljkovic et al. (2009) "Methylprednisolone Inhibits IFN-Y and IL-17 Expression and Production by Cells Infiltrating Central Nervous System in Experimental Autoimmune Encephalomyelitis", Journal of Neuroinflammation, 6(37):10 Pages.
Minn et al. (Jul. 28, 2005) "Genes that Mediate Breast Cancer Metastasis to Lung", Nature, 436(7050):518-524(15 pages).
Mohler et al. (May 1996) "Androgen and Glucocorticoid Receptors in the Stroma and Epithelium of Prostatic Hyperplasia and Carcinoma", Clinical Cancer Research, 2(5):889-895.
Möller et al. (May 2010) "Impact of New Technologies for Cellular Screening Along The Drug Value Chain", Drug Discovery Today, 15(9/10):384-390.
Moran et al. (Feb. 15, 2000) "The Glucocorticoid Receptor Mediates a Survival Signal in Human Mammary Epithelial Cells1", Cancer Research, 60(4):867-872.
Moses et al. (2007) "The Growing Applications of Click Chemistry", Chemical Society Reviews, 36:1249-1262.
Mottet et al. (2011) "EAU Guidelines on Prostate Cancer. Part II: Treatment of Advanced, Relapsing, and Castration-Resistant Prostate Cancer", European Urology, 59(4):572-583.
Munhoz et al. (2006) "Chronic Unpredictable Stress Exacerbates Lipopolysaccharide-Induced Activation of Nuclear Factor-kappaB in the Frontal Cortex and Hippocampus Via Glucocorticoid Secretion", The Journal of Neuroscience, 26(14):3813-3820.
Munster et al. (2018) "A Phase 1/2 Study of Relacorilant + Nab-Paclitaxel (Nabpac) in Patients (Pts) with Solid Tumors: The Dose-Finding Phase", Journal of Clinical Oncology, 36(15):4 Pages.
Niemeier et al. (2010) "Androgen Receptor in Breast Cancer: Expression in Estrogen Receptor-Positive Tumors and in Estrogen Receptor-Negative Tumors with Apocrine Differentiation", Modern Pathology, 23:205-212.
Norman et al. (1994) "Functional Glucocorticoid Receptor Modulates Pancreatic Carcinoma Growth through an Autocrine Loop", Journal of Surgical Research, 57(1):33-38.
Novotny et al. (2003) "Cancer Therapy: New Targets for Chemotherapy", Hematology, 8(3):129-137.
Ocana et al. (2011) "Preclined Development of Molecular-targeted Agents for Cancer", Nature Reviews Clinical Oncology review, 8(4):200-209.
Ohlmann et al. (2012) "Novel Options for the Treatment of Castration-Resistant Prostate Cancer", World Journal of Urology, 30(4):495-503.
Orayj et al. (2019) "Patterns and Determinants of Prescribing for Parkinson's Disease: A Systematic Literature Review", Parkinson's Disease, Review Article ID 9237181, 2019:9237181;1-40.
Pan et al. (2011) "Activation of the Glucocorticoid Receptor is Associated with Poor Prognosis in Estrogen Receptor-Negative Breast Cancer", Cancer Research, 71(20): 6360-6370.
Pan et al. (Mar. 25, 2010) "Identification of Glucocorticoid Receptor (GR) Signatures in Primary Human Breast Cancer: Association with Relapse-Free Survival Time", Poster Presented by S.D. Conzen as a Short Talk, presented at Nuclear Receptors: Signaling, Gene Regulation and Cancer, Keystone Symposia on Molecular and Cellular Biology, Keystone Resort, Keystone, Colorado,, 1 page.
Pang et al. (2006) "Dexamethasone Decreases Xenograft Response to Paclitaxel Through Inhibition of Tumor Cell Apoptosis", Cancer Biology & Therapy, 5(8):933-940.

Panigrahi et al. (2018) "Gelucire: A versatile polymer for modified release drug delivery system", Future Journal of Pharmaceutical Sciences, 4:102-108.
Patacchioli et al. (Dec. 2003) "Adrenal Dysregulation in Amyotrophic Lateral Sclerosis", Journal of Endocrinological Investigation, 26(12):RC23-25.
Peeters et al. (Dec. 2008) "Differential Effects of the New Glucocorticoid Receptor Antagonist ORG 34517 and RU486 (Mifepristone) on Glucocorticoid Receptor Nuclear Translocation in the AtT20 Cell Line", Annals of the New York Academy of Sciences, 1148:536-541.
Perini et al. (Feb. 1, 1992) "Effects of Carbarnazepine on Pituitary-Adrenal Function in Healthy Volunteers", The Journal of Clinical Endocrinology and Metabolism, 74(2):406-412.
Petrov et al. (Mar. 2017) "ALS Clinical Trials Review: 20 Years of Failure. Are we Any Closer to Registering a New Treatment?", Frontiers in Aging Neuroscience, 9(68):1-11 pages.
Petrylak et al. (Apr. 19, 2006) "Evaluation of Prostate-Specific Antigen Declines for Surrogacy in Patients Treated on SWOG 99-16", Journal of the National Cancer Institute, 98(8):516-521.
Pike et al. (Jan. 1, 1993) "Estrogens, Progestogens, Normal Breast Cell Proliferation, and Breast Cancer Risk", Epidemiologic Review, 15(1):17-30.
Pomara et al. (May 2002) "Mifepristone (RU 486) for Alzheimer's Disease", Neurology, 58(9):1436-1437.
Pound et al. (May 5, 1999) "Natural History of Progression after PSA Elevation Following Radical Prostatectomy", JAMA, 281(17):1591-1597.
Rakotomamonjy et al. (Jan. 12, 2019) "Brain-Derived Neurotrophic Factor is Required for the Neuroprotective Effect of Mifepristone on Immature Purkinje Cells in Cerebellar Slice Culture", International Journal of Molecular Sciences, 20(2):9 Pages.
Rauhala et al. (Dec. 2005) "Dual-Specificity Phosphatase 1 and Serum/Glucocorticoid-Regulated Kinase are Downregulated in Prostate Cancer", International Journal of Cancer, 117(5):738-745.
Ring et al. (Dec. 2004) "Mechanisms of Tamoxifen Resistance", Endocrine-Related Cancer, 11(4):643-658.
Robinson et al. (2009) "Octahydrophenanthrene-2,7-diol Analogues as Dissociated Glucocorticoid Receptor Agonists: Discovery and Lead Exploration", Journal of Medicinal Chemistry, 52(6):1731-1743.
Roozendaal et al. (Jan. 2012) "The Cortisol Awakening Response in Amyotrophic Lateral Sclerosis is Blunted and Correlates with Clinical Status and Depressive Mood", Psychoneuroendocrinology, 37(1):20-26.
Rosner et al. (Dec. 2007) "Higher Tumor to Benign Ratio of the Androgen Receptor mRNA Expression Associates with Prostate Cancer Progression after Radical Prostatectomy", Urology, 70(6):1225-1229.
Sahoo et al. (Nov. 2005) "Coordinate Expression of the PI3-Kinase Downstream Effectors Serum and Glucocorticoid-Induced Kinase (SGK-1) and Akt-1 in Human Breast Cancer", Journal of Cancer, 41(17):2754-2749.
Sahu et al. (Mar. 2013) "FoxA1 Specifies Unique Androgen and Glucocorticoid Receptor Binding Events in Prostate Cancer Cells", Cancer Research, 73(5):1570-1580.
Schenone et al. (2013) "Target Identification and Mechanism of Action in Chemical Biology and Drug Discovery", Nature Chemical Biology, 9(4):232-240.
Scher et al. (Apr. 2010) "Antitumour Activity of Mdv3100 in Castration-Resistant Prostate Cancer: A Phase 1-2 Study", Lancet, 375(9724):1437-1446.
Scher et al. (Nov. 10, 2005) "Biology of Progressive, Castration-Resistant Prostate Cancer: Directed Therapies Targeting the Androgen-Receptor Signaling Axis", Journal of Clinical Oncology, 23(32):8253-8261.
Scher et al. (Sep. 20, 2011) "End Points and Outcomes in Castration-Resistant Prostate Cancer: From Clinical Trials to Clinical Practice", Journal of Clinical Oncology, 29(27):3695-3704.
Schlossmacher et al. (Oct. 2011) "Glucocorticoid Receptor-Mediated Apoptosis: Mechanisms of Resistance in Cancer Cells", Journal of Endocrinology, 211(1):17-25.

(56) References Cited

OTHER PUBLICATIONS

Segovia-Mendoza et al. (Jan. 27, 2015) "Antihormonal Agents as a Strategy to Improve the Effect of Chemo-Radiation in Cervical Cancer: In Vitro and in Vivo Study", BMC Cancer, 15(21):1-11.
Seruga et al. (Jan. 2011) "Drug Resistance in Metastatic Castration-Resistant Prostate Cancer", Nature Reviews Clinical Oncology, 8(1):12-23.
Shanmugam et al. (Oct. 12, 2007) "Serum/Glucocorticoid-Induced Protein Kinase-1 Facilitates Androgen Receptor-Dependent Cell Survival", Cell Death & Differentiation, 14(12):2085-2094.
Sharma et al. (Apr. 2010) "Cell Line-based Platforms to Evaluate the Therapeutic Efficacy of Candidate Anticancer Agents", Nature Reviews Cancer, 10(4):241-253.
Sherk et al. (Sep. 15, 2008) "Development of a Small Molecule Serum and Glucocorticoid-Regulated Kinase 1 Antagonist and its Evaluation as a Prostate Cancer Therapeutic", Cancer Research, 68(18):7475-7483(20 pages).
Sims et al. (Sep. 21, 2008) "The Removal of Multiplicative, Systematic Bias Allows Integration of Breast Cancer Gene Expression Datasets—Improving Meta-Analysis and Prediction of Prognosis", BMC Medical Genomics, 1(42):1-14.
Smith et al. (Dec. 4, 2002) "Expression of Glucocorticoid and Progesterone Nuclear Receptor Genes in Archival Breast Cancer Tissue", Breast Cancer Research, 5(1):R9-12.
Smith et al. (Sep. 18, 2007) "Progesterone, Glucocorticoid, but not Estrogen Receptor mRNA is Altered in Breast Cancer Stroma", Cancer Letters, 255(1):77-84.
Song et al. (Sep. 2014) "Dihydrotestosterone Enhances Castration-Resistant Prostate Cancer Cell Proliferation through STAT5 Activation via Glucocorticoid Receptor Pathway", The Prostate, 74(12):1240-1248.
Sorlie et al. (Sep. 11, 2001) "Gene Expression Patterns of Breast Carcinomas Distinguish Tumor Subclasses with Clinical Implications", Proceedings of the National Academy of Sciences of the United States of America, 98(19):10869-10874.
Sotiriou et al. (Feb. 15, 2006) "Gene Expression Profiling in Breast Cancer: Understanding the Molecular Basis of Histologic Grade to Improve Prognosis", Journal of the National Cancer Institute, 98(4):262-272.
Spataro et al. (Nov. 2015) "Plasma Cortisol Level in Amyotrophic Lateral Sclerosis", Journal of the Neurological Sciences, 358:282-286.
Srinivas et al. (May 1, 2006) "Phase II Study Evaluating Oral Triamcinolone in Patients with Androgen-Independent Prostate Cancer", Urology, 67(5):1001-1006.
Srinivas et al. (Aug. 2002) "Proteomics for Cancer Biomarker Discovery", Clinical Chemistry, 48(8):1160-1169.
Stephenson et al. (May 17, 2006) "Preoperative Nomogram Predicting the 10-Year Probability of Prostate Cancer Recurrence After Radical Prostatectomy", Journal of the National Cancer Institute, 98(10):715-717.
Sterbis et al. (Feb. 1, 2008) "Higher Expression of the Androgen-Regulated Gene PSA-HK3 mRNA in Prostate Cancer Tissues Predicts Biochemical Recurrence-Free Survival", Clinical Cancer Research, 14(3):758-763.
Stringer-Reasor et al. (Sep. 2015) "Glucocorticoid Receptor Activation Inhibits Chemotherapy-Induced Cell Death in High-Grade Serous Ovarian Carcinoma", Gynecologic Oncology, 138(3):656-662.
Sui et al. (Jun. 1, 2007) "Estrogen Receptor a Mediates Breast Cancer Cell Resistance to Paclitaxel through Inhibition of Apoptotic Cell Death", Cancer Research., 67(11):5337-5344.
Sun et al. (Aug. 2010) "Castration Resistance in Human Prostate Cancer Is Conferred by a Frequently Occurring Androgen Receptor Splice Variant", Journal of Clinical Investigation, 120(8):2715-2730.
Sundahl et al. (Jul. 2016) "Selective Glucocorticoid Receptor-Activating Adjuvant Therapy in Cancer Treatments", Oncoscience, 3(7-8):188-202.
Szmulewitz et al. (Feb. 1, 2012) "Serum/Glucocorticoid-Regulated Kinase 1 Expression in Primary Human Prostate Cancers", Prostate, 72(2):157-164.
Tannock et al. (Oct. 7, 2004) "Docetaxel Plus Prednisone or Mitoxantrone Plus Prednisone for Advanced Prostate Cancer", The New England Journal of Medicine, 351(15):1502-1512.
Taplin et al. (May 2008) "A Phase II Study of Mifepristone (Ru-486) in Castration-Resistant Prostate Cancer, with a Correlative Assessment of Androgen-Related Hormones", BJU International, 101(9):1084-1089.
Tessier et al. (Aug. 15, 2006) "Serum and Glucocorticoid-Regulated Protein Kinases: Variations on a Theme", Journal of Cellular Biochemistry, 98(6):1391-1407.
Tokuda et al. (May 14, 2002) "Prednisolone (30-60 Mg/Day) for Diseases Other than AD Decreases Amyloid B-peptides in CSF", Neurology, 58(9):1415-1418.
Touat et al. (Oct. 2014) "Successful Treatment of Multiple Intracranial Meningiomas with the Antiprogesterone Receptor Agent Mifepristone (RU486)", Acta Neurochirurgica, 156(10):1831-1835.
Twiddy et al. (Mar. 2011) "Cholesterol as a Potential Target for Castration-Resistant Prostate Cancer", Pharmaceutical Research, 28(3):423-437.
Venkatesh et al. (Feb. 2000) "Role of the Development Scientist in Compound Lead Selection and Optimization", Journal of Pharmaceutical Sciences, 89(2):145-154.
Wang et al. (Feb. 19-25, 2005) "Gene-Expression Profiles to Predict Distant Metastasis of Lymph-Node-Negative Primary Breast Cancer", The Lancet, 365(9460):671-679.
Ward et al. (Apr. 1, 2005) "Rising Prostate-Specific Antigen after Primary Prostate Cancer Therapy", Nature Clinical Practice Urology, 2(4):174-182.
Wayne Genck (2004) Chemical Processing.com.
West et al. (Feb. 2016) "Abstract PD3-02: Second-generation selective glucocorticoid receptor modulators in triple-negative breast cancer", Cancer Research, Poster Discussion Abstracts, Thirty-Eighth Annual CTRC-AACR, 76(4 Supplement):PD3-02 (2 pages).
Wright et al. (Dec. 2009) "Differences in Prostate Cancer Outcomes Between Cases With Gleason 4+3 and Gleason 3+4 Tumors in a Population Based Cohort", The Journal of Urology, 182(6):2702-2707.
Wu et al. (Oct. 1, 2006) "Glucocorticoid Receptor Activation Signals through Forkhead Transcription Factor 3a in Breast Cancer Cells", Molecular Endocrinology, 20(10):2304-2314.
Wu et al. (Mar. 1, 2004) "Microarray Analysis Reveals Glucocorticoid-Regulated Survival Genes that are Associated with Inhibition of Apoptosis in Breast Epithelial Cells", Cancer Research, 64(5):1757-1764.
Wu et al. (Aug. 16, 2004) "Prevalent Expression of the Immunostimulatory MHC Class I Chain-Related Molecule Is Counteracted by Shedding in Prostate Cancer", Journal of Clinical Investigation, 114(4):560-568.
Yemelyanov et al. (Jan. 15, 2012) "Differential Targeting of Androgen and Glucocorticoid Receptors Induces ER Stress and Apoptosis in Prostate Cancer Cells", Cell Cycle, 11(2):395-406.
Yemelyanov et al. (Mar. 22, 2007) "Tumor Suppressor Activity of Glucocorticoid Receptor in the Prostate", Oncogene, 26(13):1885-1896.
Yu et al. (Jan. 19, 2015) "Systems Pharmacology of Mifepristone (RU486) Reveals its 47 Hub Targets and Network: Comprehensive Analysis and Pharmacological Focus on FAK-Src-Paxillin Complex", Scientific Reports, 5(1):7830(1-10).
Yves Fradet (May 2009) "Biomarkers In Prostate Cancer Diagnosis And Prognosis: Beyond Prostate-Specific Antigen", Current Opinion in Urology, 19(3);243-246.
Zegarra-Moro et al. (Feb. 15, 2002) "Disruption of Androgen Receptor Function Inhibits Proliferation of Androgen-refractory Prostate Cancer Cells", Cancer Research, 62(4):1008-1013.
Zhang et al. (Mar. 15, 2006) "Corticosteroid Co-Treatment Induces Resistance to Chemotherapy in Surgical Resections, Xenografts and Established Cell Lines of Pancreatic Cancer", BMC Cancer, 6(61):1-14.

(56) References Cited

OTHER PUBLICATIONS

Zou et al. (Apr. 2009) "Androgen-Induced Coactivator ANCCA Mediates Specific Androgen Receptor Signaling in Prostate Cancer", Cancer Research, 69(8):3339-3346.

* cited by examiner

FORMULATIONS OF DAZUCORILANT, A GLUCOCORTICOID RECEPTOR MODULATOR

CROSS-REFERENCE TO RELATED APPLICATIONS

This application claims priority to U.S. Provisional Application No. 63/378,578, filed Oct. 6, 2022, which is incorporated by reference herein in its entirety for all purposes.

BACKGROUND

In most species, including man, the physiological glucocorticoid is cortisol (hydrocortisone). Glucocorticoids are secreted in response to ACTH (corticotropin), which shows both circadian rhythm variation and elevations in response to stress and food. Cortisol levels are responsive within minutes to many physical and psychological stresses, including trauma, surgery, exercise, anxiety and depression. Cortisol is a steroid and acts by binding to an intracellular, glucocorticoid receptor (GR). A mineralocorticoid receptor (MR), also known as a type I glucocorticoid receptor (GR I), binds cortisol, and may also be activated by aldosterone in humans. Compositions including modulators of one or both of GR and MR may be used to treat a variety of diseases and disorders. In man, GR may be present in two forms: a ligand-binding GR-alpha of 777 amino acids; and, a GR-beta isoform which lacks the 50 carboxy terminal residues. Since these residues include the ligand binding domain, GR-beta is unable to bind the natural ligand, and is constitutively localized in the nucleus.

The biologic effects of cortisol, including those caused by hypercortisolemia, can be modulated at the GR level using receptor modulators, such as agonists, partial agonists and antagonists. Several different classes of agents are able to inhibit the physiologic effects of GR-agonist binding. These antagonists include compositions which, by binding to GR, inhibit the ability of an agonist to effectively bind to and/or activate the GR. One such known GR antagonist, mifepristone, has been found to be an effective anti-glucocorticoid agent in humans (Bertagna (1984) J. Clin. Endocrinol. Metab. 59:25). Mifepristone binds to the GR with high affinity, with a dissociation constant (Kd) of $10^{-9}$ M (Cadepond (1997) Annu. Rev. Med. 48:129).

In addition to cortisol, the biological effects of other steroids can be modulated at the GR level using receptor modulators, such as agonists, partial agonists and antagonists. When administered to subjects in need thereof, steroids can provide both intended therapeutic effects as well as negative side effects.

Amyotrophic lateral sclerosis (ALS) is a rare and devastating disease with insufficient treatment options. It is characterized by progressive degeneration of motor neurons in both the brain and the spinal cord leading to progressive muscle weakness, relentless disability and, generally, death within 3-5 years from symptom onset. Only a small percentage of patients survive more than 10 years. Fifty percent of patients die within 30 months of symptom onset; approximately 20% survive 5-10 years after onset (Riva N, Agosta F, Lunetts C, Filippi M, Quattrini A. 2016. Recent advances in amyotrophic lateral sclerosis. J. Neurol. 263:1241-1254). Respiratory failure is the most common cause of mortality in patients with ALS (Riva et al. 2016; Turner M R, Hardman O, Benatar M, Brooks B R, Chio A, de Carvalho M, et al. 2013. Controversies and priorities in amyotrophic lateral sclerosis. Lancet Neurol. 12:310-322). Familial ALS accounts for 10% of cases, with sporadic ALS accounting for the remaining 90% of cases (Van Damme P, Robberecht W, Van Den Bosch L. 2017. Modelling amyotrophic lateral sclerosis: progress and possibilities. Dis. Model. Mech. 10:537-549).

The compounds of U.S. Pat. No. 8,859,774 have demonstrated utility for treating this condition. What is needed are new forms of these compositions. Surprisingly, the present invention meets these and other needs.

BRIEF SUMMARY OF THE INVENTION

In one embodiment, the present invention provides a composition comprising:

Compound I, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone

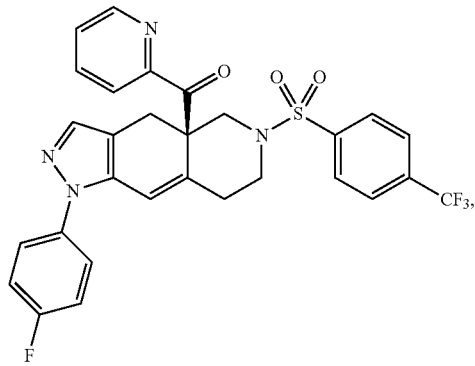 [SMILES: O=C(c1ccccn1)[C@]12Cc3cnn(-c4ccc(F)cc4)c3C=C1CCN(S(=O)(=O)c1ccc(C(F)(F)F)cc1)C2]

in an amount of from 1 to 25% (w/w); a cosolvent, in an amount of from 1 to 25% (w/w); and a surfactant, in an amount of from 50 to 90% (w/w).

In another embodiment, the present invention provides a unit dosage form for oral administration, consisting essentially of a capsule containing a composition of the present invention.

In another embodiment, the present invention provides a method of treating a disorder or condition through modulating a glucocorticoid receptor, comprising administering to a subject in need of such treatment, a therapeutically effective amount of a composition of the present invention, thereby treating the disorder or condition.

In another embodiment, the present invention provides a method of treating a disorder or condition through antagonizing a glucocorticoid receptor, comprising administering to a subject in need of such treatment, a therapeutically effective amount of a composition of the present invention, thereby treating the disorder or condition.

In another embodiment, the present invention provides a method of treating amyotrophic lateral sclerosis (ALS), comprising administering to a subject in need thereof, a therapeutically effective amount of a composition of the present invention, thereby treating ALS.

In another embodiment, the present invention provides a method of treating Alzheimer's disease, comprising administering to a subject in need thereof, a therapeutically effective amount of a composition of the present invention, thereby treating Alzheimer's.

In another embodiment, the present invention provides a method of treating Huntington's disease, comprising administering to a subject in need thereof, a therapeutically effective amount of a composition of the present invention, thereby treating Huntington's.

DETAILED DESCRIPTION OF THE INVENTION

I. General

Disclosed herein are formulations of Compound I, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone:

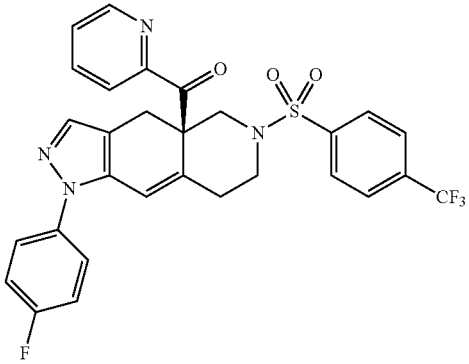 [SMILES: O=C(c1ccccn1)[C@]12Cc3cnn(-c4ccc(F)cc4)c3C=C1CCN(S(=O)(=O)c1ccc(C(F)(F)F)cc1)C2]

with a cosolvent and a surfactant.

II. Definitions

"About" refers to plus or minus 5% of the specified value unless otherwise indicated.

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier(s), diluent(s) or excipient(s) must be compatible with the other ingredients of the formulation and not deleterious to the recipient thereof.

"Cosolvent" refers to a component in a composition that improves the solubility and miscibility of other components in the composition.

"Surfactant" refers to any agent that alters the surface properties between two liquids, or between a liquid and a solid. Surfactants useful in the present invention include, but are not limited to, a non-ionic surfactant, a cationic surfactant, an anionic surfactant, an amphoteric surfactant, an ampholytic surfactant or salts thereof. A surfactant's hydrophilic/lipophilic balance (HLB) describes the surfactant's affinity toward water or oil (1-20, with 1 being lipophilic and 20 being hydrophilic). The HLB of a blend of two surfactants equals the weight fraction of surfactant A times its HLB value plus the weight fraction of surfactant B times its HLB value (weighted average). Anionic surfactants useful in the present invention include, but are not limited to soaps including alkali soaps, such as sodium, potassium and ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride and quarternary ammonium compounds such as benzalkonium chloride. Non-ionic surfactants useful in the present invention include but are not limited to polyoxyethylene castor oil derivatives, polysorbates, sorbitan esters, polyoxyethylene alkyl ethers, poloxamers and vitamin E derivatives. One of skill in the art will appreciate that other surfactants are useful in the present invention "Pharmaceutically acceptable excipient" refers to a substance that aids the administration of an active agent to and absorption by a subject. Pharmaceutical excipients useful in the present invention include, but are not limited to, oils, fatty acid esters, cosolvents, surfactants, cosurfactants and antioxidants. One of skill in the art will recognize that other pharmaceutical excipients are useful in the present invention.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Administering" refers to oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, horse, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Fridrun and Jones, *Pharmaceutical Capsules*, (2004), Lieberman, *Pharmaceutical Dosage Forms* (Disperse Systems vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20$^{th}$ Edition, 2003, Gennaro, Ed., Lippincott, Williams & Wilkins).

"Glucocorticoid receptor" ("GR") refers to one of the family of intracellular receptors which specifically bind to cortisol and/or cortisol analogs such as dexamethasone (See, e.g., Turner & Muller, J. Mol. Endocrinol. Oct. 1, 2005 35 283-292). The glucocorticoid receptor is also referred to as the cortisol receptor. The term includes isoforms of GR, recombinant GR and mutated GR.

A cortisol receptor is a glucocorticoid receptor (GR), specifically the type II GR, which specifically binds cortisol and/or cortisol analogs such as dexamethasone (See, e.g., Turner & Muller, J. Mol. Endocrinol. Oct. 1, 2005 35 283-292).

"Mineralocorticoid receptor" (MR) refers to a type I glucocorticoid receptor (GR I), which is activated by aldosterone in humans.

"Glucocorticoid receptor modulator" (GRM) refers to any compound which modulates any biological response associated with the binding of a glucocorticoid receptor to an agonist. As used herein, with respect to a GRM, the glucocorticoid receptor may be GR, or both. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, inhibits the agonist-induced increase in the activity of tyrosine aminotransferase (TAT) in HepG2 cells. TAT activity can be measured as outlined in the literature by A. Ali et al., J. Med. Chem., 2004, 47, 2441-2452.

"Glucocorticoid receptor antagonist" (GRA) refers to any compound which inhibits any biological response associated with the binding of a glucocorticoid receptor to an agonist. As used herein, with respect to a GRA, the glucocorticoid receptor may be GR, or both. Accordingly, GR antagonists can be identified by measuring the ability of a compound to inhibit the effect of dexamethasone. TAT activity can be measured as outlined in the literature by A. Ali et al., J. Med. Chem., 2004, 47, 2441-2452. An inhibitor is a compound with an $IC_{50}$ (half maximal inhibition concentration) of less than 10 micromolar.

"Modulate" and "modulating" are used in accordance with its plain ordinary meaning and refer to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

"Modulator" refers to a composition that increases or decreases the level of a target molecule or the function of a target molecule or the physical state of the target of the molecule.

"Antagonize' and "antagonizing" refer to inhibiting the binding of an agonist at a receptor molecule or to inhibiting the signal produced by a receptor-agonist. A receptor antagonist inhibits or dampens agonist-mediated responses, such as gene expression.

"Antagonist" refers to a substance capable of detectably lowering expression or activity of a given gene or protein. The antagonist can inhibit expression or activity 10%, 20%, 30%, 40%, 50%, 60%, 70%, 80%, 90%, 100% or less in comparison to a control in the absence of the antagonist. In some embodiments, the inhibition is 1.5-fold, 2-fold, 3-fold, 4-fold, 5-fold, 10-fold, or more than the expression or activity in the absence of the antagonist.

"Inhibition", "inhibits" and "inhibitor" refer to a compound that prohibits or a method of prohibiting, a specific action or function.

"Disorder" or "condition" refers to a state of being or health status of a patient or subject capable of being treated with the glucocorticoid receptor modulator of the present invention.

"Amyotrophic lateral sclerosis", "ALS" and "Lou Gehrig's disease" refers to group of neurodegenerative diseases characterized by the loss of motor neurons in the ventral horns of the spinal cord and the cortical neurons that provide their afferent input. ALS can initially affect principally either the upper or lower motor neurons, but irrespective of the primary lesion area, with time, the disease acquires a symmetrical generalized nature (Mitsumoto, H. et al. Amyotrophic Lateral Sclerosis, In Contemporary Neurology Series 49, Philadelphia, F. A. Davis Company (1998)). Both sporadic and familial forms of ALS occur with familial ALS, usually autosomal dominant, representing about 10% of ALS (Dion P A et al., Nat. Rev. Genet. 10:769-782 (2009)). ALS symptoms typically appear earlier in familial cases, but the clinical courses of familial and sporadic forms are comparable. Several types of genetic mutations have been identified as causative for the development of familial ALS with approximately 20% of the familial cases caused by inherited mutations in the protein Cu/Zn superoxide dismutase (SOD1) that protects motor neurons from free radical damage (Rosen D R et al., Nature, 362:59-62 (1993)).

Unlike some forms of familial ALS, the specific the etiology of sporadic ALS remains elusive with different hypotheses proposed including glutamate-mediated excitotoxicity, impaired mitochondrial function, oxidative stress, neuroinflammation and aberrant protein aggregation (Dib M, Drugs, 63: 289-310 (2003); Strong M J, Pharmacology & Therapeutics, 98:379-414 (2003); Bruijn L I et al., Annu. Rev. Neurosci, 27:723-749 (2004); Dibernardo A B et al., Biochimica et Biophysica Acta, 1762:1139-1149 (2006)).

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

III. Compositions

The present invention provides pharmaceutically acceptable compositions of (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone (Compound I; see Example 1 of U.S. Pat. No. 8,859,774) which provide surprisingly improved solubility and stability of the composition. Compound I is practically insoluble in water and difficult to solubilize in most dosage forms that would be suitable for pharmaceutical use; routine methods have proven unsuccessful in providing pharmaceutically acceptable compositions of this compound. Compositions prepared by routine methods, even if able to solubilize small amounts of Compound I, have proven unstable with Compound I falling out of solution, or in which Compound I is found to be subject to rapid degradation, or incompatible with a pharmaceutically acceptable capsule. Surprisingly, the compositions disclosed herein overcome the previous problems of solubility and bioavailability, and provide pharmaceutically acceptable compositions with enhanced solubility and bioavailability, suitable for use in treating conditions and disorders amenable to treatment by administration of Compound I.

The compositions of the present invention are Type IV compositions according to the Lipid Formulation Classification System (LFCS). The LFCS identifies the characteristics of lipid systems (C. W. Pouton, Eur. J. Pharm. Sci., 11 (Suppl. 2) (2000), pp. S93-S98). As classified in the LFCS, Type I formulations are oils which require digestion, Type II formulations are water-insoluble self-emulsifying drug delivery systems (SEDDS), Type III systems are SEDDS or self-micro emulsifying drug delivery systems (SMEDDS) or self-nano emulsifying drug delivery systems (SNEDDS) which contain some water-soluble surfactants and/or co-solvents (Type IIIA) or a greater proportion of water soluble components (Type IIIB). Type IV systems represent formulations which contain predominantly hydrophilic surfactants and co-solvents that disperse and dissolve in aqueous media to provide a solution. A further description of the Lipid Formulation Classification System can also be found in FABAD J. Pharm. Sci., pages 55-64, 2013.

The present invention provides compositions of (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone (Compound I; CORT113176; dazucorilant; see Example 1 of U.S. Pat. No. 8,859,774). In some embodiments, the present invention provides a composition including Compound I having the structure:

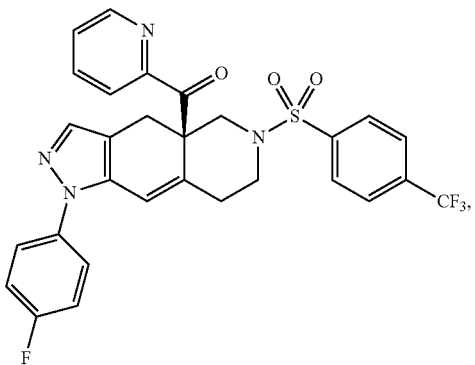 [SMILES: O=C(c1ccccn1)[C@]12Cc3cnn(-c4ccc(F)cc4)c3C=C1CCN(S(=O)(=O)c1ccc(C(F)(F)F)cc1)C2]

and a pharmaceutically acceptable excipient.

In some embodiments, the present invention provides a composition comprising: Compound I, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone:

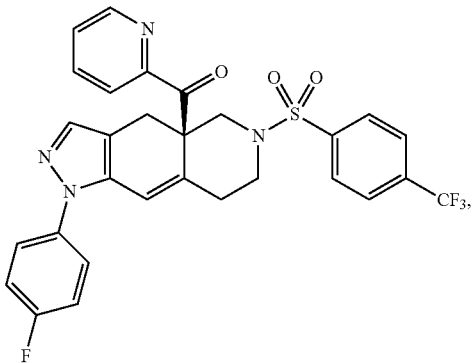 [SMILES: O=C(c1ccccn1)[C@]12Cc3cnn(-c4ccc(F)cc4)c3C=C1CCN(S(=O)(=O)c1ccc(C(F)(F)F)cc1)C2]

in an amount of from 1 to 25% (w/w); a cosolvent, in an amount of from 1 to 25% (w/w); and a surfactant, in an amount of from 50 to 90% (w/w).

Compound I

Compound I can be present in the composition of the present invention in any suitable relative amount. For example, Compound I can be present in the composition of the present invention in an amount of from 1 to 50% (w/w), or from 1 to 25%, or from 5 to 40%, or from 10 to 30%, or from 10 to 25%, or from 13 to 22%, or from 10 to 20%, or from 15 to 20%, or from 13 to 17%, or from 14 to 16%, or from 18 to 22%, or from 18 to 20%, or from 18 to 22%, or from 19 to 21% (w/w). Representative amounts of Compound I in the compositions of the present invention include, but are not limited to, about 10% (w/w), or about 11, 12, 13, 14, 15, 16, 17, 18, 19, 20, 21, 22, 23, 24, or about 25% (w/w). Other amounts of Compound I useful in the compositions of the present invention include about 18.0% (w/w), or about 18.1, 18.2, 18.25, 18.3, 18.4, 18.5, 18.6, 18.7, 18.75, 18.8, 18.9, or about 19.0% (w/w).

In some embodiments, the compositions of the present invention include the composition wherein Compound I is present in an amount of from 1 to 25% (w/w). In some embodiments, the compositions of the present invention include the composition wherein Compound I is present in an amount of from 10 to 25% (w/w). In some embodiments, the compositions of the present invention include the composition wherein Compound I is present in an amount of from 15 to 20% (w/w). In some embodiments, the compositions of the present invention include the composition wherein Compound I is present in an amount of from 13 to 22% (w/w). In some embodiments, the compositions of the present invention include the composition wherein Compound I is present in an amount of from 15 to 20% (w/w). In some embodiments, the compositions of the present invention include the composition wherein Compound I is present in an amount of from 18 to 20% (w/w).

In some embodiments, the compositions of the present invention include the composition wherein Compound I is present in an amount of about 15% (w/w). In some embodiments, the compositions of the present invention include the composition wherein Compound I is present in an amount of about 18.75% (w/w). In some embodiments, the compositions of the present invention include the composition wherein Compound I is present in an amount of about 20% (w/w).

Compound I can be present in the composition of the present invention in any suitable absolute amount. For example, Compound I can be present in the composition of the present invention in an amount of from 1 to 500 mg, or 10 to 400 mg, or from 20 to 300 mg, or from 30 to 200 mg, or from 40 to 100 mg, or from 50 to 100 mg, or from 55 to 90 mg, or from 60 to 90 mg, or from 55 to 85 mg, or from 70 to 80 mg, or from 72 to 78 mg, or from 74 to 76 mg. Representative amounts of Compound I in the compositions of the present invention include, but are not limited to, about 10 mg, or 15, 20, 25, 30, 35, 40, 45, 50, 55, 60, 65, 70, 75, 80, 85, 90, 95, or about 100 mg. Other representative amounts of Compound I in the compositions of the present invention include, but are not limited to, about 55 mg, or 56, 57, 58, 59, 60, 61, 62, 63, 64, 65, 66, 67, 68, 69, 70, 71, 72, 73, 74, 75, 76, 77, 78, 79, 80, 81, 82, 83, 84, or about 85 mg. Other representative amounts of Compound I in the compositions of the present invention include, but are not limited to, about 50 mg, 75 mg, 100 mg, or about 150 mg.

In some embodiments, the compositions of the present invention include the composition wherein Compound I is present in an amount of from 50 to 150 mg. In some embodiments, the compositions of the present invention include the composition wherein Compound I is present in an amount of from 50 to 100 mg. In some embodiments, the compositions of the present invention include the composition wherein Compound I is present in an amount of from 55 to 85 mg. In some embodiments, the compositions of the present present invention include the composition wherein Compound I is present in an amount of from 55 to 65 mg. In some embodiments, the compositions of the present invention include the composition wherein Compound I is present in an amount of from 70 to 80 mg. In some embodiments, the compositions of the present invention include the composition wherein Compound I is present in an amount of from 75 to 85 mg.

In some embodiments, the compositions of the present invention include the composition wherein Compound I is present in an amount of about 60 mg. In some embodiments, the compositions of the present invention include the composition wherein Compound I is present in an amount of about 75 mg. In some embodiments, the compositions of the present invention include the composition wherein Compound I is present in an amount of about 80 mg.

In some embodiments, the compositions of the present invention include the composition wherein Compound I is present in an amount of about 50 mg. In some embodiments, the compositions of the present invention include the composition wherein Compound I is present in an amount of about 75 mg. In some embodiments, the compositions of the present invention include the composition wherein Compound I is present in an amount of about 100 mg. In some embodiments, the compositions of the present invention include the composition wherein Compound I is present in an amount of about 125 mg. In some embodiments, the compositions of the present invention include the composition wherein Compound I is present in an amount of about 150 mg.

Cosolvent

The cosolvent of the compositions of the present invention can include any suitable cosolvent. For example, the cosolvent in the compositions of the present invention can include, but are not limited to, polyethylene glycols (PEG), ethanol, propylene glycol, glycerol, diethylene glycol monoethyl ether, glycofurol, triacetin, N-methyl-2-pyrrolidone, dimethylacetamide, dimethylsulfoxide, propylene glycol esters, or combinations thereof.

In some embodiments, the compositions of the present invention include the composition wherein the cosolvent includes polyethylene glycols (PEG), ethanol, propylene glycol, glycerol, diethylene glycol monoethyl ether, glycofurol, triacetin, N-methyl-2-pyrrolidone, dimethylacetamide, dimethylsulfoxide, propylene glycol esters, or combinations thereof. In some embodiments, the compositions of the present invention include the composition wherein the cosolvent comprises polyethylene glycol (PEG).

When the cosolvent of the compositions of the present invention is polyethylene glycol (PEG), the PEG can have any suitable molecular weight that is liquid or semisolid at room temperature. For example, the PEG cosolvent in the compositions of the present invention can have a molecular weight of from 100 to 5000 Daltons, or from 100 to 2500 Daltons, or from 100 to 1000 Daltons, or from 100 to 750 Daltons, or from 200 to 600 Daltons, or from 300 to 500 Daltons. Representative molecular weights of the PEG cosolvent in the compositions of the present invention include, but are not limited to, about 220 Daltons, or 260, 310, 350, 400, 440, 480, 530, 570, 620, or about 660 Daltons. In some embodiments, the compositions of the present invention include the composition wherein the cosolvent comprises polyethylene glycol having a molecular weight of about 400 Daltons (PEG400).

The cosolvent can be present in the compositions of the present invention in any suitable amount. For example, the cosolvent can be present in the compositions of the present invention in an amount of from 1 to 90% (w/w), or from 5 to 25% (w/w), or from 2 to 20%, or from 3 to 15%, or from 4 to 10%, or from 5 to 8%, or from 6 to 7% (w/w).

Representative amounts of the cosolvent in the compositions of the present invention include, but are not limited to, about 1% (w/w), or 2, 3, 4, 5, 6, 7, 8, 9, or about 10% (w/w). Other representative amounts of the cosolvent in the compositions of the present invention include, but are not limited to, about 6.1, 6.2, 6.3, 6.4, 6.5, 6.6, 6.7, 6.8, or about 6.9% (w/w).

In some embodiments, the compositions of the present invention include the composition wherein the cosolvent is present in an amount of from 1 to 25% (w/w). In some embodiments, the compositions of the present invention include the composition wherein the cosolvent comprises PEG400 in an amount of from 5 to 8% (w/w). In some embodiments, the compositions of the present invention include the composition wherein the cosolvent comprises PEG400 in an amount of from 6 to 7% (w/w). In some embodiments, the compositions of the present invention include the composition wherein the cosolvent comprises PEG400 in an amount of about 6.5% (w/w).

The cosolvent can be present in the composition of the present invention in any suitable absolute amount. For example, cosolvent can be present in the composition of the present invention in an amount of from 1 to 100 mg, or 5 to 50 mg, or from 10 to 40 mg, or from 15 to 35 mg, or from 20 to 30 mg, or from 22 to 28 mg, or from 24 to 28 mg, or from 25 to 27 mg. Representative amounts of cosolvent in the compositions of the present invention include, but are not limited to, about 15 mg, or 16, 17, 18, 19, 20, 21, 22, 23, 24, 25, 26, 27, 28, 29, 30, 31, 32, 33, 34, or about 35 mg.

In some embodiments, the compositions of the present invention include the composition wherein the cosolvent is present in an amount of from 20 to 30 mg. In some embodiments, the compositions of the present invention include the composition wherein the cosolvent is present in an amount of about 26 mg.

Surfactant

The surfactant of the compositions of the present invention can include any suitable surfactant. The surfactants of the compositions of the present invention are generally hydrophilic non ionic surfactants, and generally have an HLB value of greater than 10, or greater than 12. Other non ionic surfactants useful in the compositions of the present invention have an HLB value greater than 4. For example, the surfactant of the compositions of the present invention includes, but is not limited to, Vitamin E polyethylene glycol succinate (Vitamin E TPGS), sorbitan monooleate, sorbitan monolaurate, polysorbate 80, polysorbate 20, Solutol HS 15, poloxamer 407 or poloxamer 168, Labrafil® M-1944CS, Labrafil M-2125CS, Labrasol® (Gattefosse, Saint-Priest, Lyon, France) Softigen® 767 (IOI Oleo GmbH, Germany), Gelucires (including Gelucire 44/14, 48/16 and 50/13), Kolliphor RH40, Kolliphor® EL (also known as cremophor), Kolliphor P188, Kolliphor® HS 15, Kolliphor® RH40 is Macrogolglycerol hydroxystearate (available from SIGMA-Aldrich, St. Louis, MO, USA), or combinations thereof.

In some embodiments, the compositions of the present invention include the composition wherein the surfactant includes Vitamin E polyethylene glycol succinate (Vitamin E TPGS), polysorbate, Solutol HS 15, poloxamer 407, Labrafil® M-1944CS, Labrafil M-2125CS, Labrasol®, Softigen® 767, Gelucire, Kolliphor, or combinations thereof. In some embodiments, the compositions of the present invention include the composition wherein the surfactant comprises Vitamin E polyethylene glycol succinate (Vitamin E TPGS). In some embodiments, the compositions of the present invention include the composition comprising PEG400 and Vitamin E TPGS.

The surfactant can be present in the compositions of the present invention in any suitable amount. For example, the surfactant can be present in the compositions of the present invention in an amount of from 10 to 95% (w/w), or from 25 to 95% (w/w), or from 50 to 95% (w/w), or from 50 to 90% (w/w), or from 60 to 90% (w/w), or from 65 to 85% (w/w), or from 70 to 80% (w/w), or from 72 to 78% (w/w), or from 72 to 76% (w/w), or from 74 to 76% (w/w), or from 76 to 80% (w/w). Representative amounts of the surfactant in the compositions of the present invention include, but are not limited to, about 50% (w/w), or 55, 60, 65, 70, 75, 80, 85, 90, or about 95% (w/w). Other representative amounts of the surfactant in the compositions of the present invention include, but are not limited to, about 71, or 72, 73, 74, 75, 76, 77, 78, or about 79% (w/w). Other representative amounts of the surfactant in the compositions of the present invention include, but are not limited to, about 73.1% (w/w), or 73.2, 73.25, 73.3, 73.4, 73.5, 73.6, 73.7, 73.75, 73.8, 73.9, 74.0, 74.1, 74.2, 72.25, 74.3, 74.4, 74.5, 74.6, 74.7, 74.75, 74.8, or about 74.9% (w/w). Other representative amounts of the surfactant in the compositions of the present invention include, but are not limited to, about 78.1% (w/w), or 78.2, 78.25, 78.3, 78.4, 78.5, 78.6, 78.7, 78.75, 78.8, or about 78.9% (w/w).

In some embodiments, the compositions of the present invention include the composition wherein the surfactant is present in an amount of from 10 to 90% (w/w). In some embodiments, the compositions of the present invention include the composition wherein the surfactant is present in an amount of from 50 to 90% (w/w). In some embodiments, the compositions of the present invention include the composition wherein the surfactant comprises Vitamin E polyethylene glycol succinate (Vitamin E TPGS) in an amount of from 70 to 80% (w/w). In some embodiments, the compositions of the present invention include the composition wherein the surfactant comprises Vitamin E polyethylene glycol succinate (Vitamin E TPGS) in an amount of from 72 to 78% (w/w). In some embodiments, the compositions of the present invention include the composition wherein the surfactant comprises Vitamin E polyethylene glycol succinate (Vitamin E TPGS) in an amount of from 74 to 76% (w/w).

In some embodiments, the compositions of the present invention include the composition wherein the surfactant comprises Vitamin E polyethylene glycol succinate (Vitamin E TPGS) in an amount of about 73.5% (w/w). In some embodiments, the compositions of the present invention include the composition wherein the surfactant comprises Vitamin E polyethylene glycol succinate (Vitamin E TPGS) in an amount of about 74.75% (w/w). In some embodiments, the compositions of the present invention include the composition wherein the surfactant comprises Vitamin E polyethylene glycol succinate (Vitamin E TPGS) in an amount of about 78.5% (w/w).

The surfactant can be present in the composition of the present invention in any suitable absolute amount. For example, the surfactant can be present in the composition of the present invention in an amount of from 100 to 1000 mg, or from 100 to 500 mg, or from 150 to 450 mg, or from 200 to 400 mg, or from 250 to 350 mg, or from 275 to 325 mg. Representative amounts of surfactant in the compositions of the present invention include, but are not limited to, about 250, or 255, 260, 265, 270, 275, 280, 285, 290, 295, 300, 305, 310, 315, 320, 325, 330, 335, 340, 345, or about 350 mg. Other representative amounts of surfactant in the compositions of the present invention include, but are not limited to, about 291 mg, or 292, 293, 294, 295, 296, 297, 298, 299, 300, 301, 302, 303, 304, 305, 306, 307, 308, 309, 310, 311, 312, 313, 314, 315, 316, 317, 318, or about 319 mg.

In some embodiments, the compositions of the present invention include the composition wherein the surfactant is present in an amount of from 275 to 325 mg. In some embodiments, the compositions of the present invention include the composition wherein the surfactant is present in an amount of about 294 mg. In some embodiments, the compositions of the present invention include the composition wherein the surfactant is present in an amount of about 299 mg. In some embodiments, the compositions of the present invention include the composition wherein the surfactant is present in an amount of about 314 mg.

Combinations

In some embodiments, the compositions of the present invention include the composition including Compound I, PEG400, and Vitamin E TPGS. In some embodiments, the compositions of the present invention consisting essentially of the composition including Compound I, PEG400, and Vitamin E TPGS. In some embodiments, the compositions of the present invention include the composition consisting of Compound I, PEG400, and Vitamin E TPGS.

In some embodiments, the compositions of the present invention include the composition comprising: Compound I, in an amount of about 18.75% (w/w); PEG400, in an amount of about 6.5% (w/w); and Vitamin E TPGS, in an amount of about 74.75% (w/w). In some embodiments, the compositions of the present invention include the composition comprising: Compound I, in an amount of about 75 mg; PEG400, in an amount of about 26 mg; and Vitamin E TPGS, in an amount of about 299 mg. In some embodiments, the compositions of the present invention include the composition consisting of: Compound I, in an amount of 75 mg; PEG400, in an amount of 26 mg; and Vitamin E TPGS, in an amount of 299 mg.

In some embodiments, the compositions of the present invention include the composition comprising: Compound I, in an amount of about 50 mg; PEG400, in an amount of about 17 mg; and Vitamin E TPGS, in an amount of about 200 mg. In some embodiments, the compositions of the present invention include the composition consisting of: Compound I, in an amount of 50 mg; PEG400, in an amount of 17 mg; and Vitamin E TPGS, in an amount of 200 mg.

In some embodiments, the compositions of the present invention include the composition comprising: Compound I, in an amount of about 75 mg; PEG400, in an amount of about 26 mg; and Vitamin E TPGS, in an amount of about 299 mg. In some embodiments, the compositions of the present invention include the composition consisting of: Compound I, in an amount of 75 mg; PEG400, in an amount of 26 mg; and Vitamin E TPGS, in an amount of 299 mg.

In some embodiments, the compositions of the present invention include the composition comprising: Compound I, in an amount of about 100 mg; PEG400, in an amount of about 35 mg; and Vitamin E TPGS, in an amount of about 399 mg. In some embodiments, the compositions of the present invention include the composition consisting of: Compound I, in an amount of 100 mg; PEG400, in an amount of 35 mg; and Vitamin E TPGS, in an amount of 399 mg.

In some embodiments, the compositions of the present invention include the composition comprising: Compound I, in an amount of about 125 mg; PEG400, in an amount of about 43 mg; and Vitamin E TPGS, in an amount of about 498 mg. In some embodiments, the compositions of the present invention include the composition consisting of: Compound I, in an amount of 125 mg; PEG400, in an amount of 43 mg; and Vitamin E TPGS, in an amount of 498 mg.

In some embodiments, the compositions of the present invention include the composition comprising: Compound I, in an amount of about 150 mg; PEG400, in an amount of about 52 mg; and Vitamin E TPGS, in an amount of about 598 mg. In some embodiments, the compositions of the present invention include the composition consisting of: Compound I, in an amount of 150 mg; PEG400, in an amount of 52 mg; and Vitamin E TPGS, in an amount of 598 mg.

In some embodiments, the compositions of the present invention include the composition comprising: Compound I, in an amount of about 15% (w/w); PEG400, in an amount of about 6.5% (w/w); and Vitamin E TPGS, in an amount of about 78.5% (w/w). In some embodiments, the compositions of the present invention include the composition comprising: Compound I, in an amount of about 60 mg; PEG400, in an amount of about 26 mg; and Vitamin E TPGS, in an amount of about 314 mg. In some embodiments, the compositions of the present invention include the composition consisting of: Compound I, in an amount of about 60 mg; PEG400, in an amount of about 26 mg; and Vitamin E TPGS, in an amount of about 314 mg. In some embodiments, the compositions of the present invention include the composition consisting of: Compound I, in an amount of 60 mg; PEG400, in an amount of 26 mg; and Vitamin E TPGS, in an amount of 314 mg.

In some embodiments, the compositions of the present invention include the composition comprising: Compound I, in an amount of about 20.0% (w/w); PEG400, in an amount of about 6.5% (w/w); and Vitamin E TPGS, in an amount of about 73.5% (w/w). In some embodiments, the compositions of the present invention include the composition comprising: Compound I, in an amount of about 80 mg; PEG400, in an amount of about 26 mg; and Vitamin E TPGS, in an amount of about 294 mg. In some embodiments, the compositions of the present invention include the composition consisting of: Compound I, in an amount of about 80 mg; PEG400, in an amount of about 26 mg; and Vitamin E TPGS, in an amount of about 294 mg. In some embodiments, the compositions of the present invention include the composition consisting of: Compound I, in an amount of 80 mg; PEG400, in an amount of 26 mg; and Vitamin E TPGS, in an amount of 294 mg.

The compositions of the present invention can be prepared and administered in a wide variety of oral dosage forms, including but not limited to, liquid filled capsules or solution products for oral or enteral administration. Other oral preparations include tablets, pills, powder, dragees, capsules, slurries, suspensions, etc., suitable for ingestion by the patient. Accordingly, the present invention also provides pharmaceutical compositions including one or more pharmaceutically acceptable carriers and/or excipients and either a compound, or a pharmaceutically acceptable salt of a compound.

For preparing compositions from Compound I, pharmaceutically acceptable carriers can be either solid, semisolid or liquid. A solid carrier can be one or more substances, which may also act as solubilizers, emulsifier, dispersing agents, antioxidants, or an encapsulating material. Details on techniques for formulation and administration are well described in the scientific and patent literature, see, e.g., the 23$^{rd}$ edition of Remington's Pharmaceutical Sciences, Maack Publishing Co, Easton PA ("Remington's").

Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

The pharmaceutical preparation can be prepared in a unit dosage form. In such form the preparation is subdivided into unit doses containing appropriate quantities of the active component. The unit dosage form can be a packaged preparation, the package containing discrete quantities of preparation, such as packeted capsules or solutions in bottles, vials or blister packs The composition of the present invention can be in a unit dosage form. The unit dosage form of the compositions of the present invention can be of any suitable amount. For example, the compositions of the present invention can be in a unit dosage form of from 100 to 1000 mg, or from 200 to 750 mg, or from 250 to 750 mg, of rom 300 to 500 mg, or from 350 to 450 mg, or from 375 to 425 mg. Representative unit dosage form amounts for the compositions of the present invention include, but are not limited to, 100, 200, 250, 300, 350, 400, 450, 500, 550, 600, 650, 700, or about 750 mg. In some embodiments, the compositions of the present invention include the composition in a unit dosage form of 400 mg. In some embodiments, the compositions of the present invention include the composition in a unit dosage form of 267 mg. In some embodiments, the compositions of the present invention include the composition in a unit dosage form of 533 mg. In some embodiments, the compositions of the present invention include the composition in a unit dosage form of 667 mg. In some embodiments, the compositions of the present invention include the composition in a unit dosage form of 800 mg.

The dosage regimen also takes into consideration pharmacokinetics parameters well known in the art, i.e., the rate of absorption, bioavailability, metabolism, clearance, and the like (see, e.g., Hidalgo-Aragones (1996) *J. Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; the latest Remington's, supra). The state of the art allows the clinician to determine the dosage regimen for each individual patient, GR and/or MR modulator and disease or condition treated.

Single or multiple administrations of the compositions can be administered depending on the dosage and frequency as required and tolerated by the patient. The compounds should provide a sufficient quantity of active agent to effectively treat the disease state. Thus, in some embodiments, the pharmaceutical formulations for oral administration of the compound is in a daily amount of between about 0.5 to about 30 mg per kilogram of body weight per day. In some embodiments, dosages can be from about 1 mg to about 20 mg per kg of body weight per patient per day are used. Actual methods for preparing parenterally administrable formulations will be known or apparent to those skilled in the art and are described in more detail in such publications as Remington's, supra. See also Nieman, In "Receptor Mediated Antisteroid Action," Agarwal, et al., eds., De Gruyter, New York (1987).

In some embodiments, the pharmaceutical formulations for oral administration of the compound are in a daily amount of between about 50 mg and about 300 mg of Compound I. In some embodiments, the daily amount of Compound I is about 50 mg, about 75 mg, about 100 mg, about 150 mg, or about 300 mg. In some embodiments, the daily amount of Compound I is provided in a single unit dosage form. In some embodiments, the daily amount of Compound I is provided in two, three, or four unit dosage forms each comprising 50 mg, 75 mg, 100 mg, or 150 mg of Compound I. In some embodiments, the daily amount of Compound I is provided in two, three, or four unit dosage forms each comprising 50 mg, 75 mg, or 100 mg of Compound I. In some embodiments, the daily amount is 75 mg Compound I, provided as one unit dosage form comprising 75 mg of Compound I. In some embodiments, the daily amount is 100 mg Compound I, provided as one unit dosage form comprising 100 mg of Compound I. In some embodiments, the daily amount is 100 mg Compound I, provided as two unit dosage forms each comprising 50 mg of Compound I. In some embodiments, the daily amount is 150 mg Compound I, provided as one unit dosage form comprising 150 mg of Compound I. In some embodiments, the daily amount is 150 mg Compound I, provided as two unit dosage forms each comprising 75 mg of Compound I. In some embodiments, the daily amount is 150 mg Compound I, provided as three unit dosage forms each comprising 50 mg of Compound I. In some embodiments, the daily amount is 300 mg Compound I, provided as two unit dosage forms each comprising 150 mg of Compound I. In some embodiments, the daily amount is 300 mg Compound I, provided as three unit dosage forms each comprising 100 mg of Compound I. In some embodiments, the daily amount is 300 mg Compound I, provided as four unit dosage forms each comprising 75 mg of Compound I.

Compound I described herein can be used in combination with other active agents known to be useful in modulating a glucocorticoid receptor, or with adjunctive agents that may not be effective alone, but may contribute to the efficacy of the active agent.

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In some embodiments, the active agents can be formulated separately. In some embodiments, the active and/or adjunctive agents may be linked or conjugated to one another.

After a composition of the present invention has been formulated in one or more acceptable carriers, it can be placed in an appropriate container and labeled for treatment of an indicated condition. For administration of Compound I, such labeling would include, e.g., instructions concerning the amount, frequency and method of administration.

In some embodiments, the present invention provides a unit dosage form for oral administration, consisting essentially of a capsule containing a composition of the present invention. The capsule can be any suitable type of capsule. For example, the capsule can be a softgel capsule or a hardgel capsule. In some embodiments, the unit dosage form for oral administration of the present invention is the unit dosage form wherein the capsule is a softgel capsule or a hardgel capsule. In some embodiments, the unit dosage form for oral administration of the present invention is the unit dosage form wherein the capsule is a softgel capsule. In some embodiments, the unit dosage form for oral administration of the present invention is the unit dosage form wherein the capsule is a hardgel capsule.

In some embodiments, the unit dosage form for oral administration of the present invention is the unit dosage form consisting essentially of a softgel capsule containing the composition consisting of: Compound I, in an amount of 75 mg; polyethylene glycol having a molecular weight of about 400 Daltons (PEG400), in an amount of 26 mg; and Vitamin E polyethylene glycol succinate (Vitamin E TPGS), in an amount of 299 mg.

In some embodiments, the unit dosage form for oral administration of the present invention is the unit dosage form consisting essentially of a hardgel capsule containing the composition consisting of: Compound I, in an amount of 75 mg; polyethylene glycol having a molecular weight of about 400 Daltons (PEG400), in an amount of 26 mg; and Vitamin E polyethylene glycol succinate (Vitamin E TPGS), in an amount of 299 mg.

In some embodiments, the unit dosage form for oral administration of the present invention is the unit dosage form consisting essentially of a hardgel capsule containing the composition consisting of: Compound I, in an amount of 50 mg; polyethylene glycol having a molecular weight of about 400 Daltons (PEG400), in an amount of 17 mg; and Vitamin E polyethylene glycol succinate (Vitamin E TPGS), in an amount of 199 mg.

In some embodiments, the unit dosage form for oral administration of the present invention is the unit dosage form consisting essentially of a hardgel capsule containing the composition consisting of: Compound I, in an amount of 100 mg; polyethylene glycol having a molecular weight of about 400 Daltons (PEG400), in an amount of 35 mg; and Vitamin E polyethylene glycol succinate (Vitamin E TPGS), in an amount of 399 mg.

In some embodiments, the unit dosage form for oral administration of the present invention is the unit dosage form consisting essentially of a hardgel capsule containing the composition consisting of: Compound I, in an amount of 150 mg; polyethylene glycol having a molecular weight of about 400 Daltons (PEG400), in an amount of 52 mg; and Vitamin E polyethylene glycol succinate (Vitamin E TPGS), in an amount of 598 mg.

IV. Methods of Use

In some embodiments, the present invention provides a method of treating a disorder or condition through modulating a glucocorticoid receptor, comprising administering to a subject in need of such treatment, a therapeutically effective amount of a composition of the present invention, thereby treating the disorder or condition.

In some embodiments, the present invention provides a method of treating a disorder or condition through antagonizing a glucocorticoid receptor, comprising administering to a subject in need of such treatment, a therapeutically effective amount of a composition of the present invention, thereby treating the disorder or condition.

In some embodiments, the present invention provides methods of modulating glucocorticoid receptor activity using the techniques described herein. In some embodiments, the method includes contacting a GR with an effective amount of a composition or Compound I of the present invention, and detecting a change in GR activity.

In some embodiments, the present invention provides methods of modulating glucocorticoid receptor activity using the techniques described herein. In some embodiments, the method includes contacting a GR or both with an effective amount of a composition or Compound I of the present invention, and detecting a change in GR activity, MR activity, or both.

In some embodiments, the glucocorticoid receptor modulator is an antagonist of GR activity or MR activity, or both GR and MR activity (also referred to herein as "a glucocorticoid receptor antagonist"). A glucocorticoid receptor antagonist, as used herein, refers to any composition or compound which partially or completely inhibits (antagonizes) the binding of a glucocorticoid receptor agonist (e.g. cortisol, aldosterone, and synthetic or natural cortisol or aldosterone analogs) to a GR, thereby inhibiting any biological response associated with the binding of a GR, to the agonist.

In some embodiments, the glucocorticoid receptor modulator is a specific glucocorticoid receptor antagonist. As used herein, a specific glucocorticoid receptor antagonist refers to a composition or compound which inhibits any biological response associated with the binding of a GR to an agonist by preferentially binding to the GR rather than another nuclear receptor (NR). In some embodiments, the specific glucocorticoid receptor antagonist binds preferentially to GR rather than the androgen receptor (AR), estrogen receptor (ER) or progesterone receptor (PR). In some embodiments, the specific glucocorticoid receptor antagonist binds preferentially to GR rather than the progesterone receptor (PR). In some embodiments, the specific glucocorticoid antagonist binds preferentially to GR rather than to the androgen receptor (AR). In some embodiments, the specific glucocorticoid antagonist binds preferentially to GR rather than to the estrogen receptor (ER).

In some embodiments, the specific glucocorticoid receptor antagonist binds to the GR with an association constant (Kd) that is at least 10-fold less than the Kd for AR or PR. In some embodiments, the specific glucocorticoid receptor antagonist binds to the GR with an association constant (Kd) that is at least 100-fold less than the Kd for AR or PR. In some embodiments, the specific glucocorticoid receptor antagonist binds to the GR with an association constant (Kd) that is at least 1000-fold less than the Kd for AR, PR or ER.

In some embodiments, the present invention provides a method of treating amyotrophic lateral sclerosis (ALS), comprising administering to a subject in need thereof, a therapeutically effective amount of a composition of the present invention, thereby treating ALS.

Amyotrophic lateral sclerosis (ALS; also known as Lou Gehrig's disease) is a progressive neuromuscular condition characterized by weakness, muscle wasting, fasciculations, and increased reflexes. Approximately 30,000 Americans are currently afflicted with the disease. The annual incidence rate is one to two cases per 100,000. The disease is most commonly diagnosed in middle age and affects more men than women. ALS is characterized by adult-onset, idiopathic, progressive degeneration of spinal anterior horn cells and upper and lower motor neurons resulting in progressive muscle weakness, wasting, and fasciculations. Atrophy of the spinal anterior horn cells and replacement of the large motor neurons by fibrous astrocytes (gliosis) causes the affected anterior and lateral columns of the spinal cord to become hard, hence the term "lateral sclerosis." Typical signs and symptoms of ALS include muscle weakness, muscle wasting (atrophy), muscle fasciculations, muscle spasticity, slowness of movement, poor balance, incoordination, alterations in vocal quality, dysarthria, dysphagia, incomplete eye closure, drooling, pseudobulbar affect, and premature death.

Up to 10% of ALS is familial, usually autosomal dominant. Several causative genes are known and, of these, mutant superoxide dismutase 1 (SOD) and mutant C9orf72 (i.e., a $G_4C_2$ hexanucleotide repeat in the C9orf72 gene) are the most frequently found among familial ALS (fALS) and sporadic ALS (sALS). Several other genes are known to be causative of classical ALS, although these account for a lower percentage of cases than does mutant SOD1; these genes include mutant FUS (fused in sarcoma), mutant TAR-DBP gene leading to modifications of the TAR DNA binding protein 43 (TDP-43), and optineurin.

The clinical presentation varies, depending on the area of the nervous system that is damaged and progression of the pathologic changes. The classic presentation of ALS is insidious, progressive, asymmetric muscular weakness and atrophy along with neurologic signs, particularly fasciculations and hyperreflexia. It usually presents with problems in dexterity or gait resulting from muscle weakness. Difficulty in speaking or swallowing is the initial symptom in the bulbar form of the disease. Over a period of months or years, patients with ALS develop severe, progressive muscular weakness and other symptoms caused by loss of function in both upper and lower motor neurons. Sphincter control, sensory function, intellectual abilities and skin integrity are preserved. Patients become completely disabled, often requiring ventilatory support and gastrostomy. Death usually occurs within five years of diagnosis and is attributed to respiratory failure or cachexia. The diagnosis of ALS is clinical, based on the characteristic signs of progressive weakness, atrophy, fasciculations and hyperreflexia affecting several regions of the body. The early differential diagnosis may include musculoskeletal, neurologic or systemic conditions. The etiology of the disease is unknown. Current management involves aggressive, individualized alleviation of symptoms and complications.

Examples of disorders or conditions suitable for use with present invention include, but are not limited to, neurodegeneration, Alzheimer's disease, Huntingtons's disease, Parkinson's disease, cognition enhancement, mild cognitive impairment, psychosis, or dementia. In some embodiments, the present invention provides a method of treating Alzheimer's disease, comprising administering to a subject in need thereof, a therapeutically effective amount of a composition of the present invention, thereby treating Alzheimer's. In some embodiments, the present invention provides a method of treating Huntington's disease, comprising administering to a subject in need thereof, a therapeutically effective amount of a composition of the present invention, thereby treating Huntington's.

V. Examples

Example 1. Preparation of Compound I

Compound I can be prepared as described in U.S. Pat. No. 8,859,774 (incorporated herein in its entirety for all purposes), Example 1, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone:

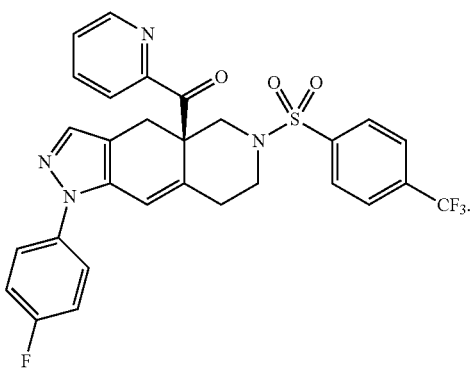 [SMILES: O=C(c1ccccn1)[C@]12Cc3cnn(-c4ccc(F)cc4)c3C=C1CCN(S(=O)(=O)c1ccc(C(F)(F)F)cc1)C2]

Example 2. Preparation of Type IV Formulations of Compound I in a Softgel Capsule Type IV formulations in softgel capsules were prepared according to the following method:

Step 1: The Vitamin E TPGS was preheated to a temperature of 65° C. until molten in a suitable oven and 74.75 g dispensed into a suitable mixing container. While maintaining a temperature of 40° C. and stirring, polyethylene glycol (6.5 g) and Compound I (18.75 g) were added to the container and the contents mixed until a visually homogeneous solution was formed. The resultant solution (fill matrix) was then deaerated, blanketed with nitrogen, and stored until encapsulation, and stored at 45-55° C. until encapsulation.

Step 2: The gel mass was prepared using gelatin, purified water, and sorbitol special glycerin blend. The gel mass was then color converted by adding titanium dioxide and red iron oxide.

Step 3: The fill matrix was encapsulated into softgel capsules.

Step 4: The capsules were dried and hardened in tumble dryers and drying chambers.

Step 5: The capsules are bulk packaged in polyethylene-lined corrugated shipping cartons.

Step 6: The capsules were packed into their final packaging configuration such as bottles or blisters.

TABLE 1

Type IV Formulation of Compound I in a Softgel Capsule, 75 mg Strength

| Component | % w/w | mg per capsule | Function |
|---|---|---|---|
| Capsule Fill Matrix | | | |
| Compound I | 18.75 | 75.0 | Active ingredient |
| Polyethylene Glycol 400 | 6.50 | 26.0 | Solubilizer & dispersion agent |
| Vitamin E TPGS | 74.75 | 299.0 | Solubilizer & surfactant |
| Total in capsule fill: | 100.0 | 400.0 | |
| Capsule Shell | | | |
| Gelatin | 63.24 | 171.43 | Capsule shell |
| Sorbitol special glycerin blend (50:50 sorbitol solution/glycerin) | 36.14 | 97.96 | Shell plasticizer |

TABLE 1-continued

Type IV Formulation of Compound I in a Softgel Capsule, 75 mg Strength

| Component | % w/w | mg per capsule | Function |
|---|---|---|---|
| Titanium dioxide | 0.49 | 1.32 | Colorant |
| Iron oxide, red | 0.14 | 0.38 | Colorant |
| Total in capsule shell: | 100.00 | 271.09 | |

TABLE 2

Type IV Formulation of Compound I, Fill matrix 60 mg Strength

| Component | % w/w | mg per capsule | Function |
|---|---|---|---|
| Compound I | 15.0 | 60.0 | Active ingredient |
| Polyethylene Glycol 400 | 6.50 | 26.0 | Solubilizer & dispersion agent |
| Vitamin E TPGS | 78.5 | 314.0 | Solubilizer & surfactant |
| Total in capsule fill: | 100.0 | 400.0 | |

TABLE 3

Type IV Formulation of Compound I, Fill matrix 80 mg Strength

| Component | % w/w | mg per capsule | Function |
|---|---|---|---|
| Compound I | 20.0 | 80.0 | Active ingredient |
| Polyethylene Glycol 400 | 6.50 | 26.0 | Solubilizer & dispersion agent |
| Vitamin E TPGS | 73.5 | 294 | Solubilizer & surfactant |
| Total in capsule fill: | 100.0 | 400.0 | |

Example 3. Preparation of Type IV Formulation of Compound I in a Hardgel Capsule, 150 mg Strength A Type IV formulation in hardgel capsules was prepared according to the following method:

Step 1: The Vitamin E TPGS was preheated to a temperature of 65° C. until molten in a suitable oven and 448.5 g was dispensed into a suitable mixing container. While maintaining a temperature of 45-55° C. and stirring, polyethylene glycol (39.0 g) and Compound I (112.5 g) were added to the container and the contents mixed until a visually homogeneous solution was formed. The resultant solution (fill matrix) was then stored at 45-55° C. until encapsulation.

Step 2: The molten fill matrix (800 mg) was encapsulated into size 00el hard gelatin capsules.

Step 3: The capsules were banded using a solution of 25% w/w gelatin. The capsules were then held on drying racks on the capsule banding equipment until dried and sealed.

Step 4: The capsules were packed into their final packaging configuration such as bottles or blisters.

TABLE 4

Type IV Formulation of Compound I, Fill
Matrix & Hardgel Capsule, 150 mg Strength

| Component | % w/w | mg per capsule | Function |
|---|---|---|---|
| Capsule Fill Matrix | | | |
| Compound I | 18.75 | 150.0 | Active ingredient |
| Polyethylene Glycol 400 | 6.50 | 52.0 | Solubilizer & dispersion agent |
| Vitamin E TPGS | 74.75 | 598.0 | Solubilizer & surfactant |
| Total in capsule fill: | 100.0 | 800.0 | |
| Capsule Shell | | | |
| Swedish Orange capsule shell size 00el | | 1 unit | Capsule shell |
| Gelatin banding[1] | | q.s | |

[1]Applied as a 25% gelatin solution. Water removed during the drying process.

Example 4. Stability Testing of Type III and IV Fill Matrices of Compound I

The Type IV fill matrix was prepared as described above, using the 18.75% w/w Compound I fill matrix shown in Table 1, and were tested under various accelerated stability conditions and compared against Type III fill matrices. For water spiked samples of Type IV formulations, 5 g water was stirred into the solution. The solution was then filled into vials while still molten and stored for in vial stability testing.

Samples of Type III formulations were prepared according to known methods using the w/w percentages in Table 5. For example, the Kolliphor ELP and Masester E8120 were preheated in a suitable oven to a temperature of 65° C. until molten. Caproyl 90 (32.24 g), Masester E8120 (24.83 g) and Kolliphor ELP (24.18 g) were added to a suitable mixing container and stirred until homogenous while maintaining a temperature of 40° C. Compound I (18.75 g) was added and mixed until dissolved and a fully homogenous solution was formed.

For samples containing antioxidants, the required amount of antioxidant was added (0.167 g of dl-alpha tocopherol or 0.02 g of BHT) and the levels of Caproyl 90, Masester E8120 and Kolliphor ELP proportionally reduced to compensate for the antioxidant present. The solution is stirred until all materials have dissolved and the solution was homogenous. For water spiked samples, 5 g water was stirred into the solution.

TABLE 5

Type III Fill Matrix Formulation

| Component (Chemical Name) | Description/ Tradename | Percentage Formula (% w/w) |
|---|---|---|
| Compound I | Drug substance | 18.75% |
| Propylene glycol monocaprylate (Type II) | Capryol 90 ® | 32.24% |
| Glyceryl caprylate/caproate | Masester E8120 ® | 24.83% |
| Polyoxyl-35 castor oil | Kolliphor ELP ® | 24.18% |
| | Total | 100.00% |

The stability of the Type IV capsule fill matrix samples was assessed as a solution in closed glass screw capped vials stored under accelerated conditions and compared to the alternative Type III formulation with or without antioxidants. For example, a 2 g quantity of each solution type were filled into 4 mL amber glass vials, the headspace nitrogen purged and the vials capped. The samples were placed in stability chambers at 30° C./65% RH and 40° C./75% RH. The assay and levels of impurities were assessed over a period of up to 12 weeks using a suitable HPLC method.

For the antioxidants in the Type III formulations either butylated hydroxytoluene (BHT) at a typical usage level of 0.02% w/w or Vitamin E (dl-alpha tocopherol) at 0.16% w/w were added with a further sample without antioxidant being evaluated. Some vials were spiked with 5% water (wet samples) to encourage degradation as it is known that moisture can migrate from capsule shells into the fill matrix during manufacture or storage. Samples that were not spiked with water (dry samples) were also assessed. For the Type IV formulation an antioxidant was not added but both wet and dry samples were assessed. Samples were stored at 40° C./75% RH and 30° C./65% RH for up to twelve weeks and the assay and total impurities determined. The results are shown in Table 6, Table 7, Table 8, and Table 9.

TABLE 6

Assay Data for Capsule Fill Matrices Stored at 30° C./60% RH

| Formulation | Antioxidant | Water Spiked | Assay (percent) after Storage at 40° C./75% RH | | | |
|---|---|---|---|---|---|---|
| | | | T = 0 | T = 4 w | T = 8 w | T = 12 w |
| Type III | Vitamin E | No | 100.7 | 98.8 | 98.8 | NA |
| | Vitamin E | Yes | 101.9 | 98.4 | 96.2 | NA |
| Type III | BHT | No | 101.1 | 98.9 | 98.8 | NA |
| | BHT | Yes | 101.3 | 97.9 | 97.0 | NA |
| Type III | None | No | 101.1 | 99.0 | 98.6 | NA |
| | None | Yes | 102.7 | 97.8 | 96.0 | NA |
| Type IV | None | No | 100.8 | 100.5 | 99.5 | 98.7 |
| | None | Yes | 102.8 | 106.3 | 101.7 | 103.4 |

NA—Not assessed

TABLE 7

Assay Data for Capsule Fill Matrices Stored at 40° C./75% RH

| Formulation | Antioxidant | Water Spiked | Assay (percent) after Storage at 40° C./75% RH | | | |
|---|---|---|---|---|---|---|
| | | | T = 0 | T = 4 w | T = 8 w | T = 12 w |
| Type III | Vitamin E | No | 100.7 | 98.0 | 97.8 | NA |
| | Vitamin E | Yes | 101.9 | 94.9 | 89.6 | NA |
| Type III | BHT | No | 101.1 | 97.8 | 97.1 | NA |
| | BHT | Yes | 101.3 | 94.2 | 89.7 | NA |
| Type III | None | No | 101.1 | 98.0 | 97.6 | NA |
| | None | Yes | 102.7 | 94.7 | 89.2 | NA |
| Type IV | None | No | 100.8 | 102.8 | 99.4 | 98.3 |
| | None | Yes | 102.8 | 106.1 | 101.7 | 98.5 |

NA—Not assessed

TABLE 8

Impurity Data for Capsule Fill Matrices Stored at 30° C./65% RH

| Formulation | Antioxidant | Water Spiked | Percentage of Total Impurities after Storage at 30° C./65% RH (% area) | | | |
|---|---|---|---|---|---|---|
| | | | T = 0 | T = 4 w | T = 8 w | T = 12 w |
| Type III | Vitamin E | No | 0.50 | 0.54 | 0.69 | NA |
| | Vitamin E | Yes | 0.50 | 1.05 | 1.28 | NA |
| Type III | BHT | No | 0.60 | 0.71 | 0.84 | NA |
| | BHT | Yes | 0.70 | 1.11 | 1.71 | NA |

TABLE 8-continued

Impurity Data for Capsule Fill Matrices Stored at 30° C./65% RH

| Formulation | Antioxidant | Water Spiked | Percentage of Total Impurities after Storage at 30° C./ 65% RH (% area) | | | |
|---|---|---|---|---|---|---|
| | | | T = 0 | T = 4 w | T = 8 w | T = 12 w |
| Type III | None | No | 0.60 | 0.64 | 0.77 | NA |
| | None | Yes | 0.60 | 1.09 | 1.69 | NA |
| Type IV | None | No | 0.50 | 0.45 | 0.48 | 0.48 |
| | None | Yes | 0.40 | 0.46 | 0.49 | 0.49 |

NA—Not assessed

TABLE 9

Impurity Data for Capsule Fill Matrices Stored at 40° C./75% RH

| Formulation | Antioxidant | Water Spiked | Percentage of Total Impurities after Storage at 40° C./ 75% RH (% area) | | | |
|---|---|---|---|---|---|---|
| | | | T = 0 | T = 4 w | T = 8 w | T = 12 w |
| Type III | Vitamin E | No | 0.50 | 0.87 | 1.25 | NA |
| | Vitamin E | Yes | 0.50 | 2.21 | 4.12 | NA |
| Type III | BHT | No | 0.60 | 1.02 | 1.45 | NA |
| | BHT | Yes | 0.70 | 2.30 | 4.22 | NA |
| Type III | None | No | 0.60 | 0.94 | 1.40 | NA |
| | None | Yes | 0.60 | 2.28 | 4.25 | NA |
| Type IV | None | No | 0.50 | 0.48 | 0.64 | 0.50 |
| | None | Yes | 0.40 | 0.61 | 0.86 | 0.92 |

NA—Not assessed

Example 5. Stability Testing of Type IV Formulations of Compound I in a Hardgel Capsule, 150 mg Strength Stability data for hardgel capsules, 150 mg strength, prepared according to the method of Example 3, was obtained. Clear 7 mL glass vials with polypropylene screw cap containing the hardgel capsules of Example 3 were stored at ambient conditions (15-25'C in the dark). The assay and levels of two key impurities (COR176-6 and CORT125863) were determined after 12 months and 24 months.

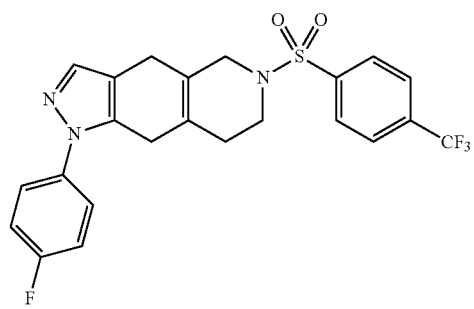

COR176-6

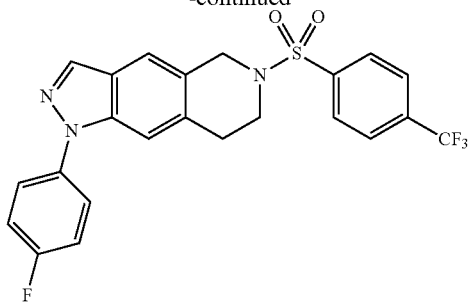

CORT125863

TABLE 10

Stability Data for Type IV Formulations of Compound I in a Hardgel Capsule, 150 mg (Glass Vials)

| Test Parameter | Initial | 12 months | 24 months |
|---|---|---|---|
| Compound I Assay (% of label claim) | 100.8 | 99.0 | 97.2 |
| COR176-6 (% area) | <0.05 | <0.05 | <0.05 |
| CORT125863 (% area) | 0.06 | 0.14 | 0.21 |
| Total Impurities (% area) | 0.5 | 0.63 | 0.77 |

No chromatographic response factor was applied for the impurities.

No chromatographic response factor was applied for the impurities.

Example 6. Preparation of Type IV Formulations of Compound I in a Hardgel Capsule, 75 mg Strength A Type IV formulation in hardgel capsules, 75 mg strength, was prepared according to the following method:

Step 1: The Vitamin E TPGS was preheated to a temperature of 60-65° C. until molten in a suitable oven and 1943.5 g was dispensed into a suitable mixing vessel. While maintaining a temperature of 40-50° C. and stirring, polyethylene glycol (169.0 g) and Compound I (487.5 g) were added to the vessel and the contents mixed until a visually homogeneous solution was formed. The resultant solution (fill matrix) was then stored at 45-55° C. until encapsulation.

Step 2: The molten fill matrix (400 mg) was encapsulated into size 0 hard gelatin capsules.

Step 3: The capsules were banded using a gelatin solution and then dried and sealed.

Step 4: The capsules were packed into their final packaging configuration in bottles. Alternative packaging such as blisters are considered.

TABLE 11

Type IV Formulation of Compound I in a Hardgel Capsule, 75 mg Strength

| Component | % w/w | mg per capsule | Function |
|---|---|---|---|
| Capsule Fill Matrix | | | |
| Compound I | 18.75 | 75.0 | Active ingredient |
| Polyethylene Glycol 400 | 6.50 | 26.0 | Solubilizer & dispersion agent |
| Vitamin E TPGS | 74.75 | 299.0 | Solubilizer & surfactant |
| Total in capsule fill: | 100.0 | 400.0 | |

TABLE 11-continued

Type IV Formulation of Compound I
in a Hardgel Capsule, 75 mg Strength

| Component | % w/w | mg per capsule | Function |
|---|---|---|---|
| Capsule Shell | | | |
| Opaque-white capsule shell size 0 | | 1 unit | Capsule shell |
| Gelatin banding[1] | | q.s | |

[1] Applied as an aqueous solution containing 21.43% w/w gelatin, 1.17% w/w polysorbate 80 and 0.87% w/w FD&C blue dye. Water removed during the drying process.

Example 7. Stability Testing of Type IV Formulation of Compound I in a Hardgel Capsule, 75 mg Strength 60 ml HPDE bottles containing 30 hardgel capsules of Example 5 were stored under ICH stability conditions. The assay and levels of the two key impurities (CR176-6 and CORT125863) were determined for up to 3 months.

TABLE 12

Room Temperature Storage (25° C./60% RH) of
Type IV Formulations of Compound I in
Hardgel Capsules, 75 mg Strength (HDPE Bottles)

| Test Parameter | Initial | 3 months |
|---|---|---|
| Compound I Assay (% of label claim) | 98.4 | 103.1 |
| COR176-6 (% w/w) | <0.05 | <0.05 |
| CORT125863 (% w/w) | 0.14 | 0.18 |
| Total Impurities (% area) | 0.59 | 0.73 |

TABLE 13

Accelerated Temperature Storage (40° C./75% RH)
of Type IV Formulations of Compound I in Hardgel
Capsules, 75 mg Strength (HDPE Bottles)

| Test Parameter | Initial | 1 month | 2 months | 3 months |
|---|---|---|---|---|
| Compound I Assay (% of label claim) | 98.4 | 99.3 | 96.7 | 97.8 |
| COR176-6 (% w/w) | <0.05 | <0.05 | 0.08 | 0.15 |
| CORT125863 (% w/w) | 0.14 | 0.21 | 0.27 | 0.35 |
| Total Impurities (% area) | 0.59 | 0.84 | 1.10 | 1.20 |

A chromatographic relative response factor (RRF) of 2.72 was applied to the COR176-6 impurity and an RRF of 1.30 applied to CORT125863.

Example 8. Preparation of Type IV Formulations of Compound I in a Softgel Capsule, 75 mg Strength Type IV formulations in softgel caspules were prepared according to the following method, and in accordance with Table 1:

Step 1: The Vitamin E TPGS was preheated to a temperature of 65° C. until molten in a suitable oven and 747.5 g dispensed into a suitable mixing container. While maintaining a temperature of 40° C. and stirring, polyethylene glycol (65.0 g) and Compound I (187.5 g) were added to the container and the contents mixed until a visually homogeneous solution was formed. The resultant solution (fill matrix) was then deaerated, blanketed with nitrogen and stored at 40-45° C. until encapsulation.

Step 2: The gel mass was prepared using gelatin, purified water, and sorbitol special glycerin blend. The gel mass was then color converted by adding titanium dioxide and red iron oxide.

Step 3: The fill matrix (400 mg) was encapsulated into softgel capsules.

Step 4: The capsules were dried and hardened in tumble dryers and drying chambers.

Step 5: Bulk capsules were packaged in polyethylene-lined corrugated shipping cartons.

Step 6: The capsules were packed into their final packaging configuration in bottles or blisters.

Example 9. Stability of Type IV Formulations of Compound I in a Softgel Capsule, 75 mg Strength Blisters containing 75 mg strength softgel capsules as provided in Example 8 were stored under ICH conditions. The assay and levels of the two key impurities (COR176-6 and CORT125863) were determined for up to 22 months at 25° C. and 60% relative humidity (RH), as shown in Table 14, and for up to 6 months at 40° C. and 75% RH as shown in Table 15.

TABLE 14

Room Temperature Storage (25° C./60% RH) Softgel Capsules 75 mg in Blisters

| Test Parameter | Timepoint (months) | | | | | | | |
|---|---|---|---|---|---|---|---|---|
| | Initial | 1 | 2 | 3 | 6 | 12 | 18 | 22 |
| Compound I Assay (% of label claim) | 104.3 | 103.5 | 104.8 | 105.4 | 104.1 | 107.0 | 102.3 | 103.1 |
| COR176-6 (% w/w) | ND | ND | 0.11 | 0.15 | 0.27 | 0.49 | 0.69 | 0.85 |
| CORT125863 (% w/w) | 0.09 | 0.12 | 0.13 | 0.15 | 0.19 | 0.28 | 0.39 | 0.44 |
| Total Impurities (% area) | 0.46 | 0.49 | 0.60 | 0.64 | 0.88 | 1.25 | 1.66 | 2.08 |

A chromatographic relative response factor has been applied to COR176-6 (2.72) and CORT125863 (1.30).

TABLE 15

Accelerated Temperature Storage (40° C./75% RH)
Softgel Capsules 75 mg Strength in Blisters

| Test Parameter | Initial | 1 month | 2 months | 3 months | 6 months |
|---|---|---|---|---|---|
| Compound I Assay (% of label claim) | 104.3 | 101.9 | 103.6 | 102.2 | 100.7 |
| COR176-6 (% w/w) | ND | 0.32 | 0.65 | 0.98 | 1.93 |
| CORT125863 (% w/w) | 0.09 | 0.22 | 0.33 | 0.44 | 0.72 |
| Total Impurities (% area) | 0.46 | 0.99 | 1.45 | 1.94 | 3.33 |

A chromatographic relative response factor has been applied to COR176-6 (2.72) and CORT125863 (1.30).

Although the foregoing invention has been described in some detail by way of illustration and example for purposes of clarity of understanding, one of skill in the art will appreciate that certain changes and modifications may be practiced within the scope of the appended claims. Where a conflict exists between the instant application and a reference provided herein, the instant application shall dominate.

What is claimed is:

1. A unit dosage form for oral administration, wherein the unit dosage form comprises a hard gelatin capsule containing a composition, the composition comprising:

Compound I, (R)-(1-(4-fluorophenyl)-6-((4-(trifluoromethyl)phenyl)sulfonyl)-4,4a,5,6,7,8-hexahydro-1H-pyrazolo[3,4-g]isoquinolin-4a-yl)(pyridin-2-yl)methanone:

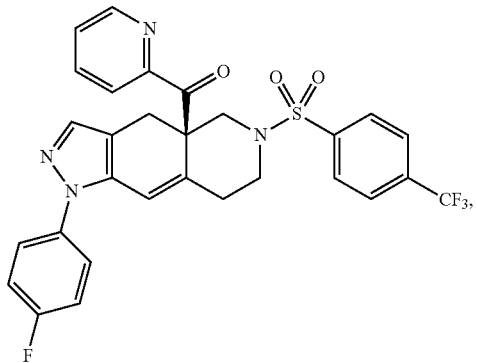 [SMILES: O=C(c1ccccn1)[C@]12Cc3cnn(-c4ccc(F)cc4)c3C=C1CCN(S(=O)(=O)c1ccc(C(F)(F)F)cc1)C2]

in an amount of about 18.75% (w/w);

polyethylene glycol having a molecular weight of about 400 Daltons (PEG400), in an amount of about 6.5% (w/w); and Vitamin E polyethylene glycol succinate (Vitamin E TPGS), in an amount of about 74.75% (w/w).

2. The unit dosage form of claim 1, wherein Compound I is present in an amount of from about 50 mg to about 150 mg.

3. The unit dosage form of claim 1, wherein the composition comprises:
Compound I, in an amount of about 50 mg;
PEG400, in an amount of about 17 mg; and
Vitamin E TPGS, in an amount of about 199 mg.

4. The unit dosage form of claim 1, wherein the composition comprises:
Compound I, in an amount of about 75 mg;
PEG400, in an amount of about 26 mg; and
Vitamin E TPGS, in an amount of about 299 mg.

5. The unit dosage form of claim 1, wherein the composition comprises:
Compound I, in an amount of about 100 mg;
PEG400, in an amount of about 35 mg; and
Vitamin E TPGS, in an amount of about 399 mg.

6. The unit dosage form of claim 1, wherein the composition comprises:
Compound I, in an amount of about 150 mg;
PEG400, in an amount of about 52 mg; and
Vitamin E TPGS, in an amount of about 598 mg.

7. The unit dosage form of claim 1, wherein the composition consists essentially of:
Compound I, in an amount of 50 mg;
PEG400, in an amount of 17 mg; and
Vitamin E TPGS, in an amount of 199 mg.

8. The unit dosage form of claim 1, wherein the composition consists essentially of:
Compound I, in an amount of 75 mg;
PEG400 in an amount of 26 mg; and
Vitamin E TPGS in an amount of 299 mg.

9. The unit dosage form of claim 1, wherein the composition consists essentially of:
Compound I, in an amount of 100 mg;
PEG400, in an amount of 35 mg; and
Vitamin E TPGS, in an amount of 399 mg.

10. The unit dosage form of claim 1, wherein the composition consists essentially of:
Compound I, in an amount of 150 mg;
PEG400, in an amount of 52 mg; and
359, Vitamin E TPGS, in an amount of 598 mg.

* * * * *